US010610634B2

(12) United States Patent
Hasegawa et al.

(10) Patent No.: US 10,610,634 B2
(45) Date of Patent: Apr. 7, 2020

(54) BLOOD PURIFICATION APPARATUS

(71) Applicant: Nikkiso Company Limited, Tokyo (JP)

(72) Inventors: Shinya Hasegawa, Shizuoka (JP);
Kunihiko Akita, Shizuoka (JP);
Masahiro Toyoda, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 231 days.

(21) Appl. No.: 15/819,219

(22) Filed: Nov. 21, 2017

(65) Prior Publication Data

US 2018/0071449 A1 Mar. 15, 2018

Related U.S. Application Data

(63) Continuation of application No. PCT/JP2016/064868, filed on May 19, 2016.

(30) Foreign Application Priority Data

May 21, 2015 (JP) ................................ 2015-103965

(51) Int. Cl.
*A61M 1/36* (2006.01)
*A61M 39/28* (2006.01)

(52) U.S. Cl.
CPC ........ *A61M 1/3656* (2014.02); *A61M 1/3624* (2013.01); *A61M 1/3627* (2013.01);
(Continued)

(58) Field of Classification Search
CPC .............. A61M 1/3653; A61M 1/3656; A61M 1/3638; A61M 1/3639; A61M 1/3624;
(Continued)

(56) References Cited

U.S. PATENT DOCUMENTS 5,336,051 A    8/1994 Tamari
5,920,054 A    7/1999 Uber
(Continued)

FOREIGN PATENT DOCUMENTS

EP    2318073 A1    5/2011
EP    2361643 A1    8/2011
(Continued)

OTHER PUBLICATIONS

Extended European Search Report dated Dec. 17, 2018, Application No. 16796556.5.
(Continued)

*Primary Examiner* — Philip R Wiest
(74) *Attorney, Agent, or Firm* — Young Basile Hanlon & MacFarlane, P.C.

(57) ABSTRACT

A blood purification apparatus includes a blood circuit through which blood of a patient extracorporeally circulate, and a dialyzer that purifies the blood flowing in the blood circuit. The apparatus includes a pressure-change-producing device capable of applying a positive pressure or a negative pressure to distal portions of the blood circuit while an arterial puncture needle (a) and a venous puncture needle (b) are yet to be connected to the blood circuit, a pressure-change-detecting device capable of detecting pressure changes in the distal portions of the blood circuit that occur when the distal portions of the blood circuit that are under the positive pressure or the negative pressure applied by the pressure-change-producing device are connected to the arterial puncture needle (a) and the venous puncture needle (b) that are stuck in the patient, and an evaluation device capable of evaluating a state of sticking of the arterial puncture needle (a) and the venous puncture needle (b) on the basis of the pressure changes detected by the pressure-change-detecting device.

16 Claims, 13 Drawing Sheets

(52) U.S. Cl.
CPC ........ *A61M 1/3638* (2014.02); *A61M 1/3643* (2013.01); *A61M 1/3661* (2014.02); A61M 39/281 (2013.01); A61M 2205/07 (2013.01); A61M 2205/3331 (2013.01); A61M 2205/3344 (2013.01); A61M 2205/3375 (2013.01); A61M 2205/3379 (2013.01)

(58) Field of Classification Search
CPC .. A61M 1/3643; A61M 1/3647; A61M 1/367; A61M 39/281; A61M 2205/3344; A61M 2205/3375
See application file for complete search history.

(56) References Cited

U.S. PATENT DOCUMENTS

| | | | |
|---|---|---|---|
| 5,927,951 | A | 7/1999 | Tamari |
| 6,044,691 | A | 4/2000 | Kenley et al. |
| 6,374,084 | B1 | 7/2002 | Fok |
| 6,497,680 | B1 | 12/2002 | Holst |
| 6,868,720 | B2 | 3/2005 | Lobdell |
| 7,147,616 | B2 | 12/2006 | Pedrazzi et al. |
| 8,011,905 | B2 | 9/2011 | Artsyukhovich |
| 9,192,708 | B2 | 11/2015 | Iwahori et al. |
| 9,662,433 | B2 | 5/2017 | Matsuo |
| 2006/0079826 | A1 | 4/2006 | Beden et al. |
| 2009/0024070 | A1 | 1/2009 | Gelfand et al. |
| 2009/0043240 | A1 | 2/2009 | Robinson et al. |
| 2009/0312686 | A1 | 12/2009 | Sakamoto et al. |
| 2010/0168640 | A1 | 7/2010 | Kopperschmidt et al. |
| 2010/0274172 | A1 | 10/2010 | Guenther et al. |
| 2011/0139690 | A1 | 6/2011 | Akita et al. |
| 2011/0213289 | A1 | 9/2011 | Toyoda |
| 2012/0000547 | A1 | 1/2012 | Gronau et al. |
| 2012/0205312 | A1* | 8/2012 | Hogard .................. 210/646 |
| 2013/0035626 | A1 | 2/2013 | Suzuki |
| 2013/0150766 | A1 | 6/2013 | Gambro |
| 2013/0172803 | A1 | 7/2013 | Gambro |
| 2013/0292313 | A1 | 11/2013 | Fava et al. |
| 2014/0138301 | A1 | 5/2014 | Iwahori et al. |
| 2014/0219829 | A1 | 8/2014 | Matsuo et al. |
| 2015/0021244 | A1 | 1/2015 | Furuhashi et al. |
| 2015/0150136 | A1 | 5/2015 | Xie et al. |
| 2015/0238677 | A1 | 8/2015 | Akita et al. |
| 2016/0250405 | A1 | 9/2016 | Kogoshi et al. |
| 2017/0095602 | A1 | 4/2017 | Ishizaki et al. |
| 2017/0173249 | A1 | 6/2017 | Matshushita et al. |
| 2017/0312412 | A1 | 11/2017 | Mochizuki et al. |

FOREIGN PATENT DOCUMENTS

| | | |
|---|---|---|
| EP | 2535067 A1 | 12/2012 |
| EP | 2883558 A1 | 6/2015 |
| JP | S60-153138 | 10/1985 |
| JP | S64-022357 | 2/1989 |
| JP | 03-001290 | 1/1991 |
| JP | H03073162 A | 3/1991 |
| JP | H06-047090 | 2/1994 |
| JP | H08-510812 A | 11/1996 |
| JP | 2003-093503 | 4/2003 |
| JP | 2003093501 A | 4/2003 |
| JP | 2003-519539 | 6/2003 |
| JP | 2003-265601 A | 9/2003 |
| JP | 2003-290342 | 10/2003 |
| JP | 2004-016619 A | 1/2004 |
| JP | 2004-049494 | 2/2004 |
| JP | 2004-187990 | 7/2004 |
| JP | 2004313522 A | 11/2004 |
| JP | 2005-253555 A | 9/2005 |
| JP | 2006-280775 A | 10/2006 |
| JP | 2007-007435 A | 1/2007 |
| JP | 3128724 U | 1/2007 |
| JP | 2007-020962 | 2/2007 |
| JP | 2007-135885 | 6/2007 |
| JP | 2007-167108 A | 7/2007 |
| JP | 2007-282737 A | 11/2007 |
| JP | 2008-289635 A | 12/2008 |
| JP | 2009-112651 A | 5/2009 |
| JP | 2009-131412 A | 6/2009 |
| JP | 2009-525770 | 7/2009 |
| JP | 2009207706 A | 9/2009 |
| JP | 2010-273784 A | 12/2009 |
| JP | 2010-000161 A | 1/2010 |
| JP | 2010-136841 | 6/2010 |
| JP | 2010-184029 | 8/2010 |
| JP | 2010-188170 A | 9/2010 |
| JP | 2010-273693 A | 12/2010 |
| JP | 2011-030880 A | 2/2011 |
| JP | 2011161060 A | 8/2011 |
| JP | 2012-095842 | 5/2012 |
| JP | 2012-095843 A | 5/2012 |
| JP | 2012/139405 A | 7/2012 |
| JP | 2012-192099 A | 10/2012 |
| JP | 2012-192100 A | 10/2012 |
| JP | 2013027494 A | 2/2013 |
| JP | 2013027495 A | 2/2013 |
| JP | 2013-056079 A | 3/2013 |
| JP | 2014-097197 A | 5/2014 |
| JP | 2014-184108 | 10/2014 |
| WO | 94/28309 A1 | 12/1994 |
| WO | 2001/051106 | 7/2001 |
| WO | 2004/000391 | 12/2003 |
| WO | 2005/118485 A | 12/2005 |
| WO | 2007/093064 A1 | 8/2007 |
| WO | 2009/004777 | 1/2009 |
| WO | 2009/074588 A1 | 6/2009 |
| WO | 2010/011444 A1 | 1/2010 |
| WO | 2011-099521 A1 | 8/2011 |
| WO | 2012/017959 A1 | 2/2012 |
| WO | 2013/031965 A1 | 3/2013 |
| WO | 2013/151114 A1 | 10/2013 |
| WO | 2014/024972 A1 | 2/2014 |
| WO | 2014/107656 A1 | 7/2014 |
| WO | 2015/068833 A1 | 5/2015 |
| WO | 2017/186354 A1 | 11/2017 |

OTHER PUBLICATIONS

International Search Report, application No. PCT/JP2016/064868 dated Aug. 2, 2016.
Supplementary European Search Report dated Mar. 16, 2016, for Application No. PCT/JP2013071511.
Japanese Office Action, Application No. 2014-529557; dated May 10, 2017.
International Search Report, Application No. PCT/JP2013/078271, dated Jan. 21, 2014.
Potentially Related Patent Application, U.S. Appl. No. 14/186,193, published as 2014/0219829, published on Aug. 7, 2014.
Extended European Search Report dated May 22, 2017 for Application No. 14860814.4.
Extended European Search Report, Application No. 13768746.3 dated Oct. 16, 2015.
International Search Report for Application No. PCT-JP2014-079688, dated Jan. 27, 2015.
Potentially related co-pending U.S. Appl. No. 13/569,645 published as 2013/0035626.
International Search Report from the Japanese Patent Office for Application No. PCT/JP2015/068562, dated Oct. 6, 2015.
Written Opinion from the Japanese Patent Office for Application No. PCT/JP2015/068562, dated Oct. 6, 2015.
Co-pending U.S. Appl. No. 14/163,051, filed Jan. 24, 2014, published as US 2014/0138301.
Co-pending U.S. Appl. No. 14/197,329, filed Mar. 5, 2014, granted as U.S. Pat. No. 9,192,708.
Co-pending U.S. Appl. No. 15/384,993, filed Dec. 20, 2016.
Potentially related U.S. Appl. No. 14/497,369, filed Sep. 26, 2014, published as US2015/0021244 on Jan. 22, 2015.
Potentially related U.S. Appl. No. 14/615,839, filed Feb. 6, 2015, published as US2015/0151036 on Jun. 4, 2015.
Potentially related U.S. Appl. No. 15/149,247, filed May 9, 2016, published as US2016/0250405 on Sep. 1, 2016.

(56) References Cited

OTHER PUBLICATIONS

Potentially related U.S. Appl. No. 15/451,653, filed Mar. 7, 2017, published as US2017/0173249 on Jun. 22, 2017.
International Search Report from the Japanese Patent Office for Application No. PCT/JP2016/057502 dated May 31, 2016.
International Search Report from the Japanese Patent Office for Application No. PCT/JP2016/057501 dated Jun. 7, 2016.
Co-pending U.S. Appl. No. 15/697,873, filed Sep. 7, 2017.
Co-pending U.S. Appl. No. 15/697,887, filed Sep. 7, 2017.

* cited by examiner

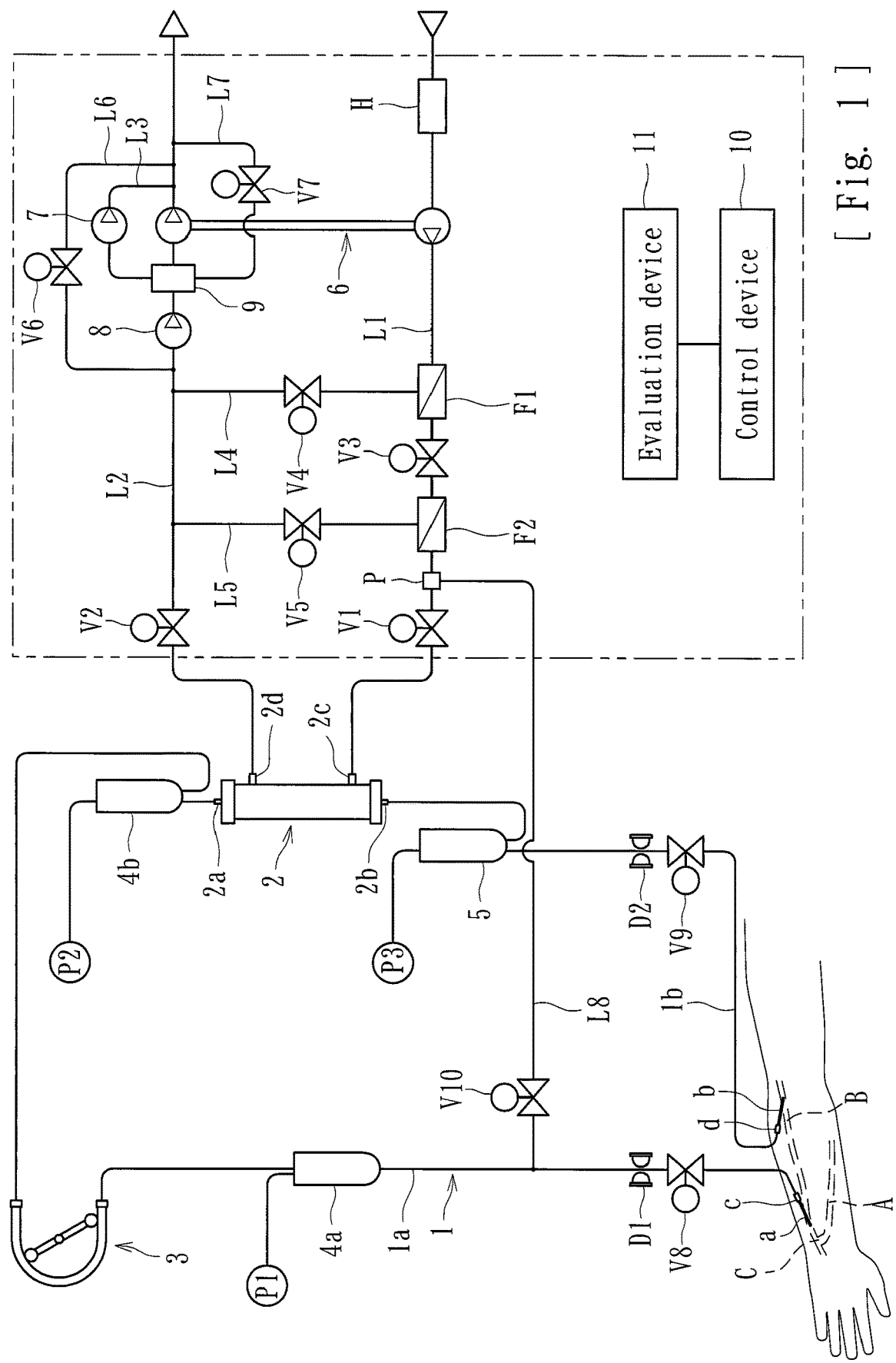
[Fig. 1]

[ Fig. 2 ]
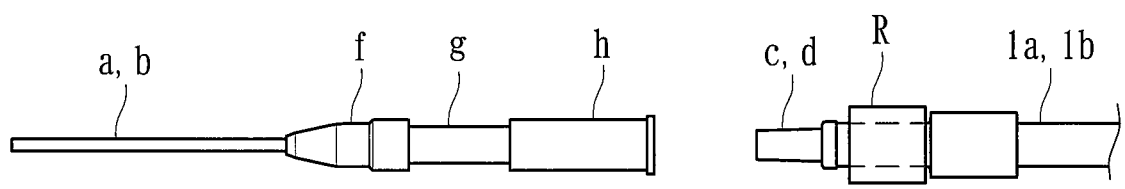
[ Fig. 3 ]
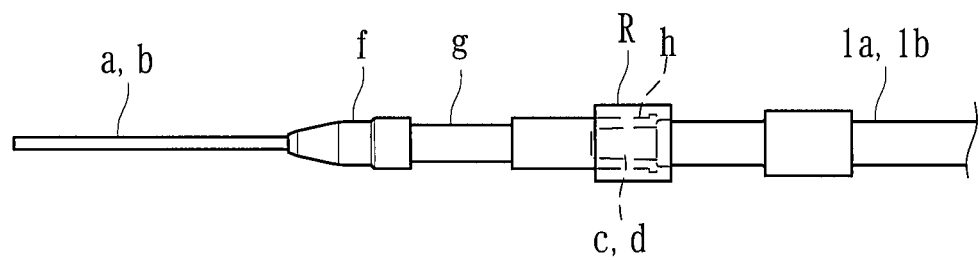

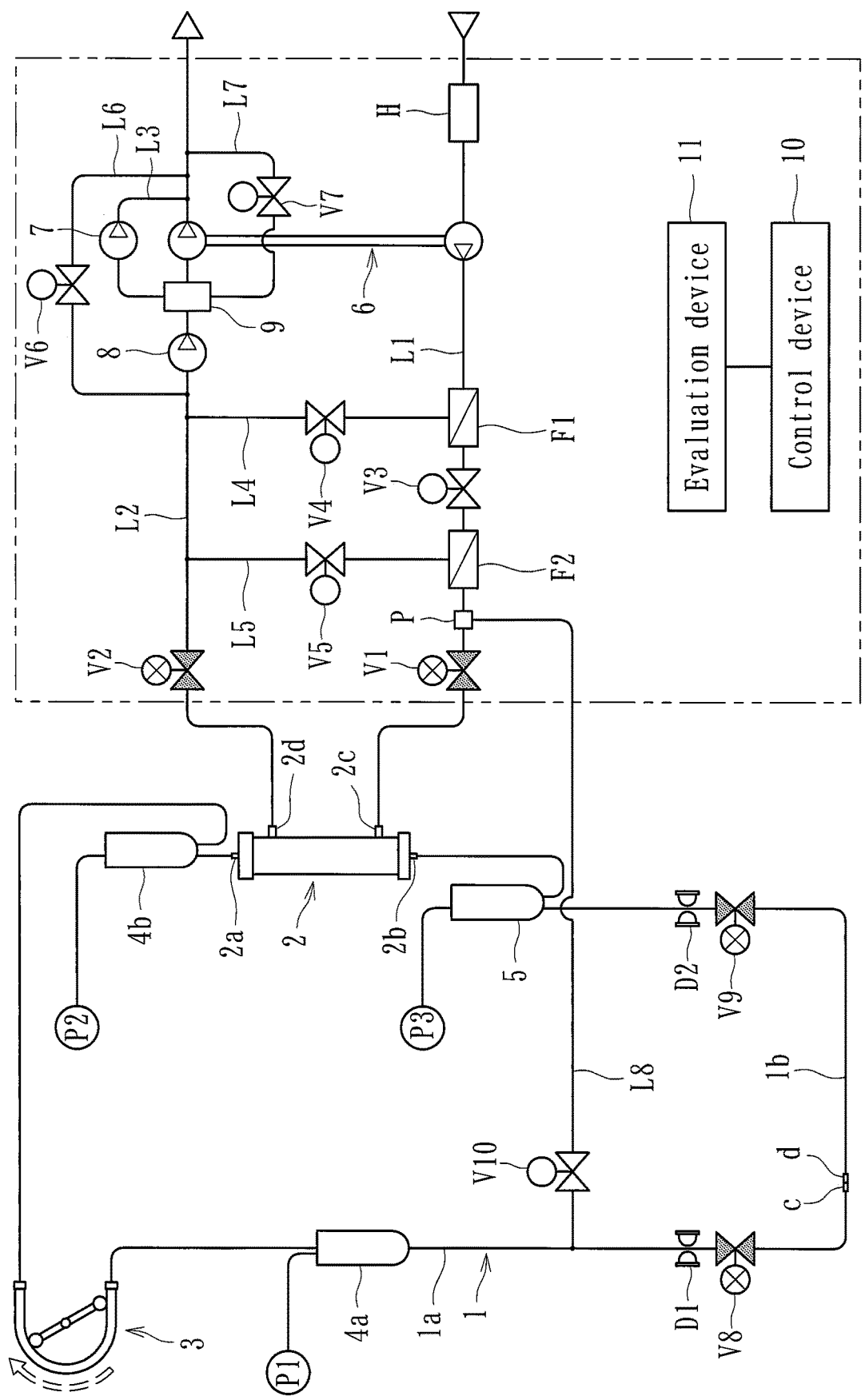
[Fig. 4]

[Fig. 5]
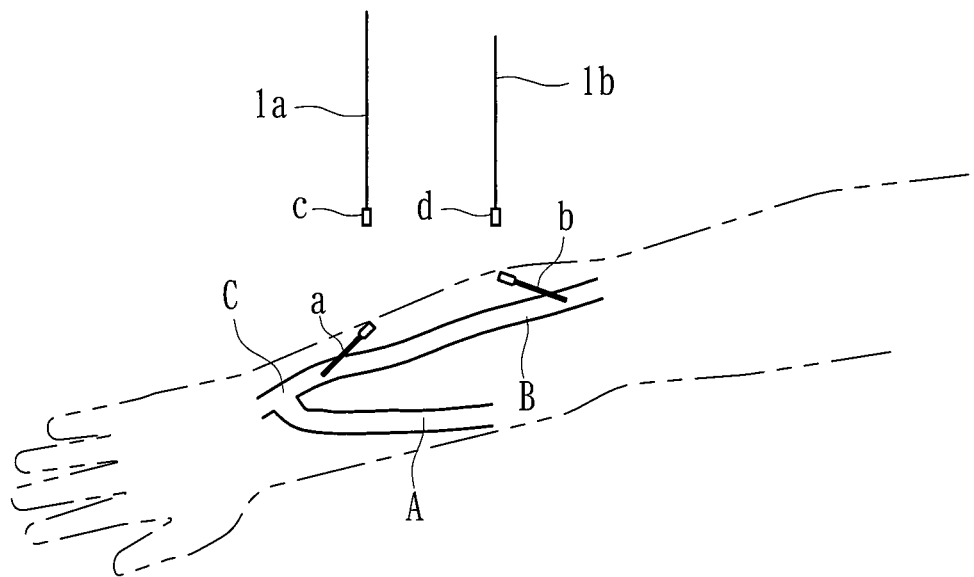
[Fig. 6]
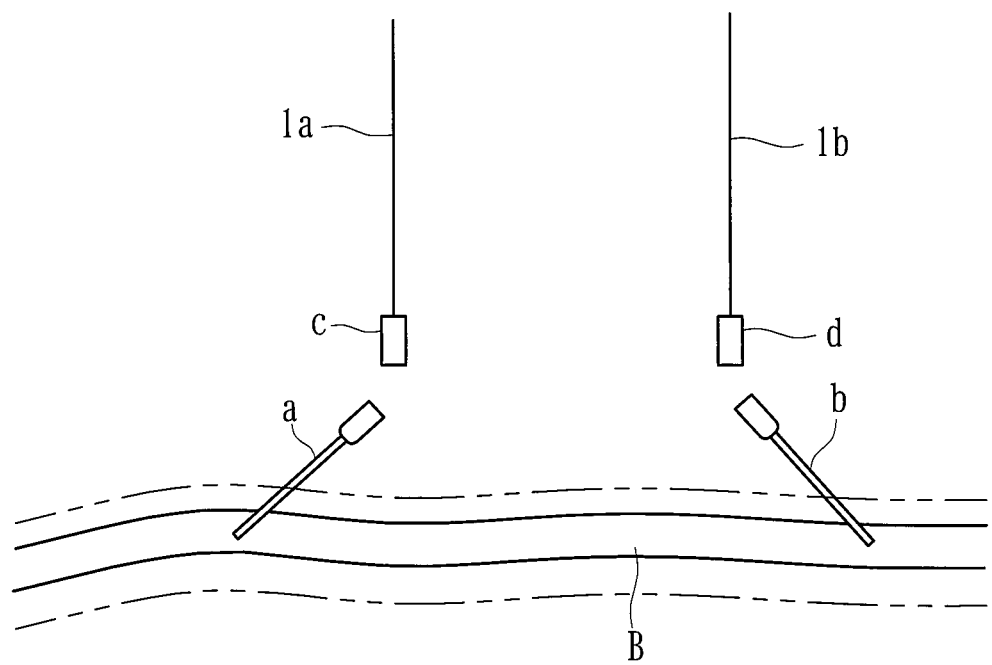

[Fig. 7]
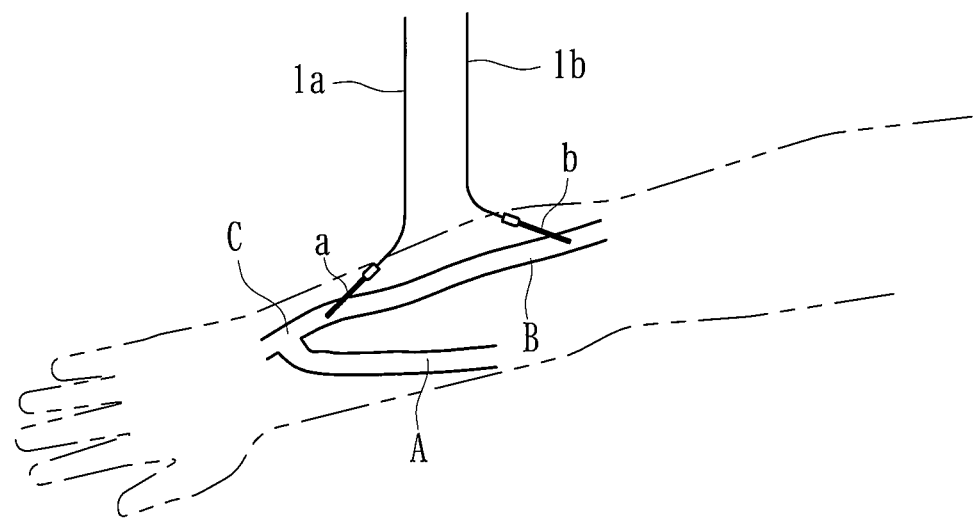
[Fig. 8]
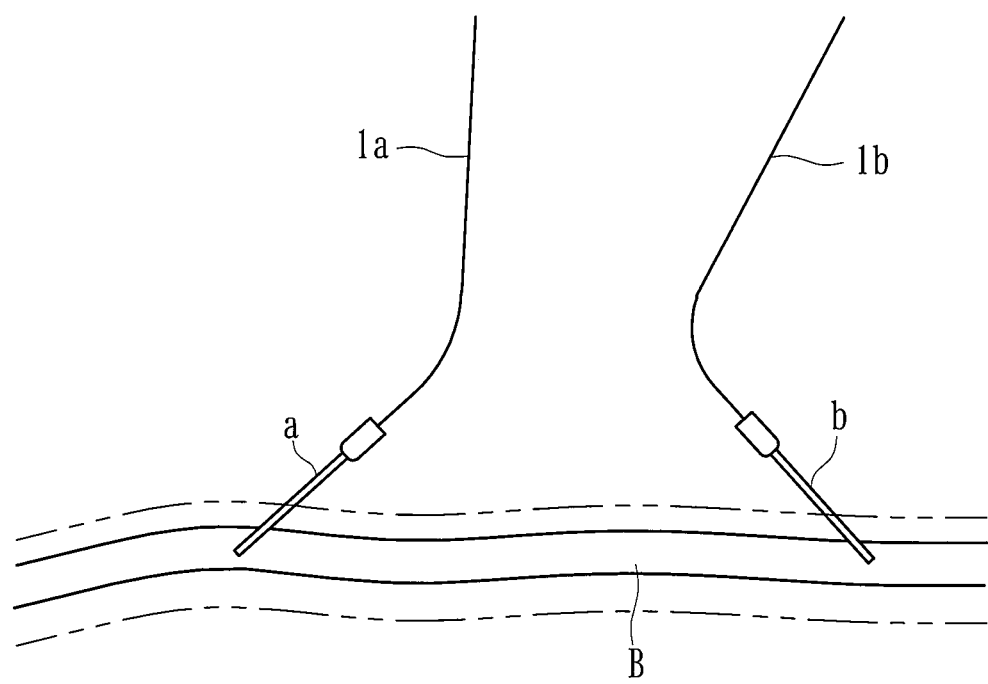

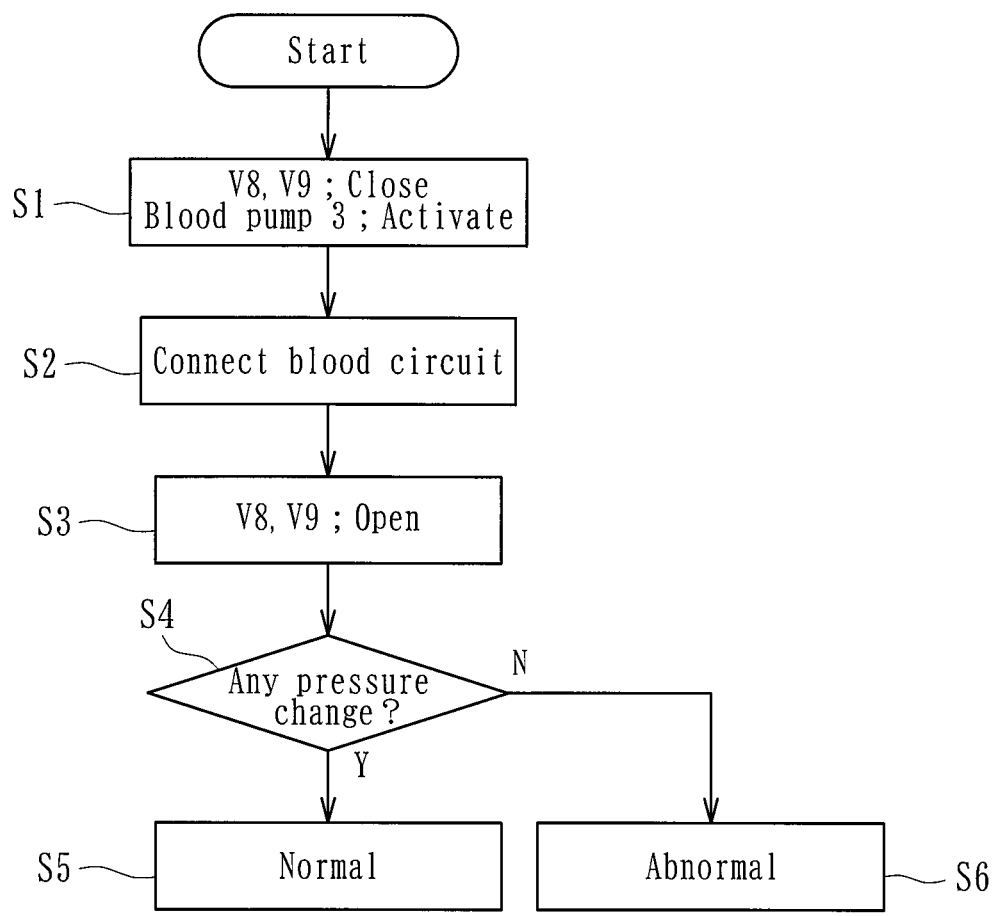
[Fig. 9]

[ Fig. 10 ]
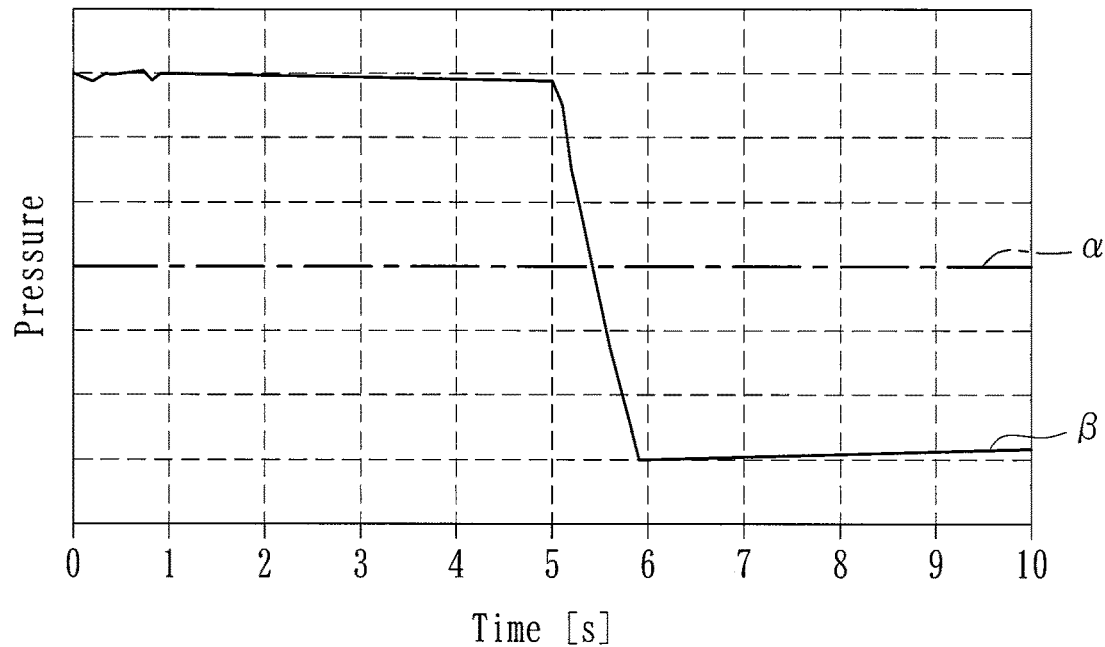
[ Fig. 11 ]
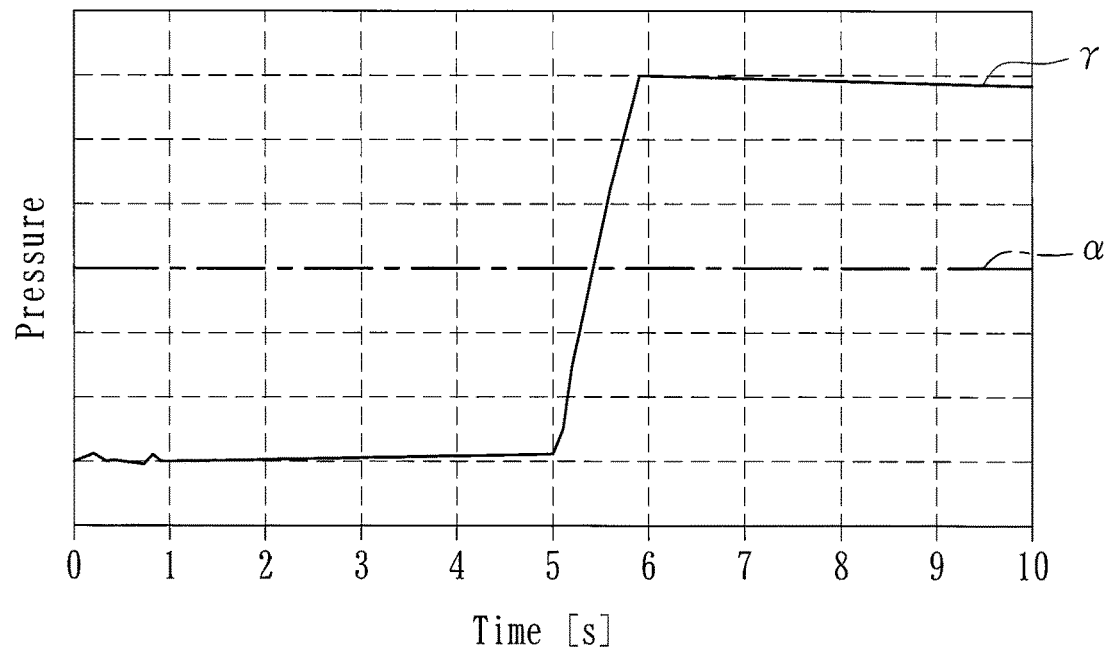

[ Fig. 12 ]
(a)
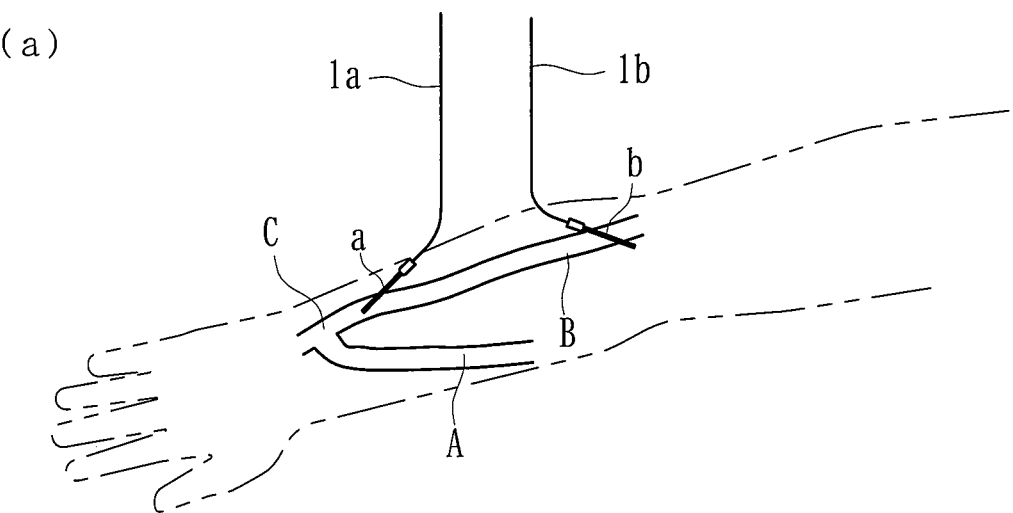
(b)
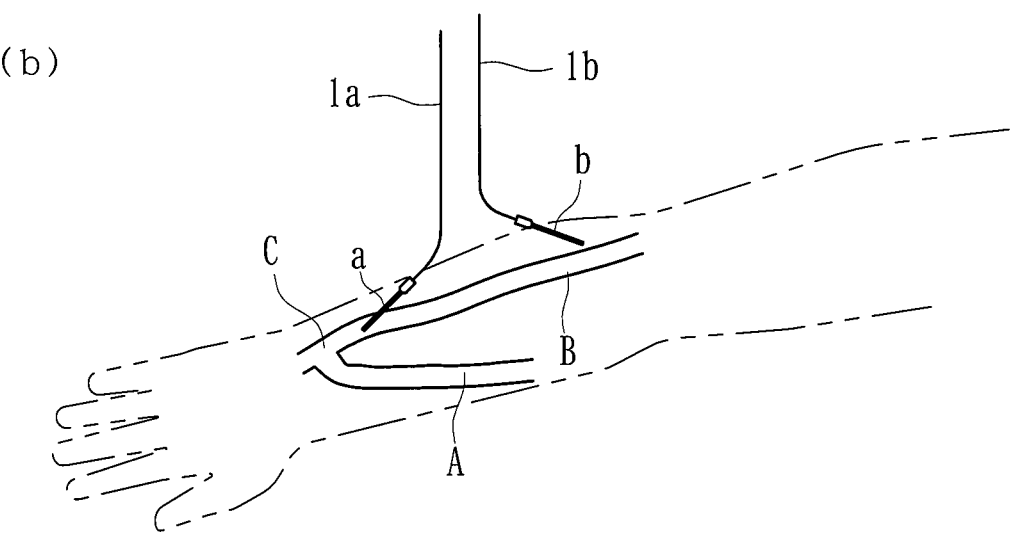

[ Fig. 13 ]
(a)
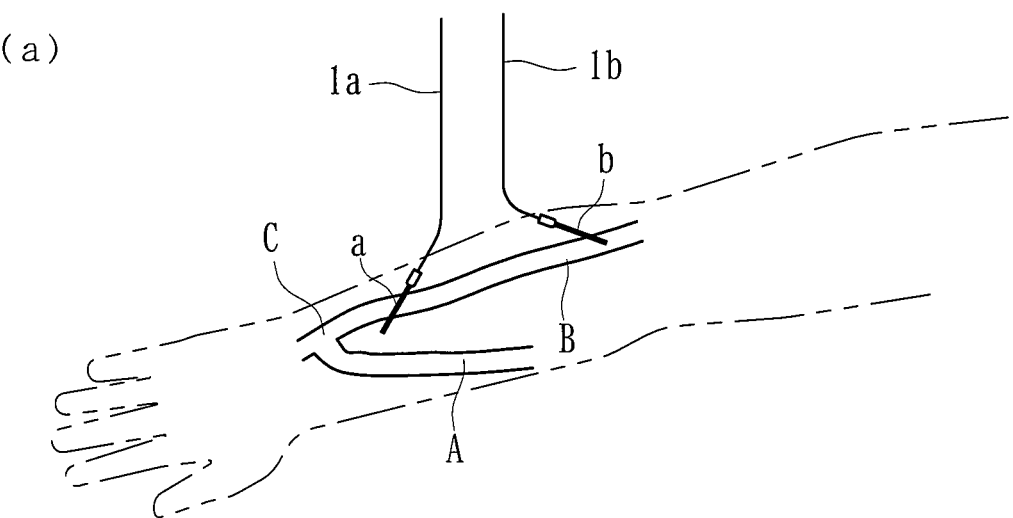
(b)
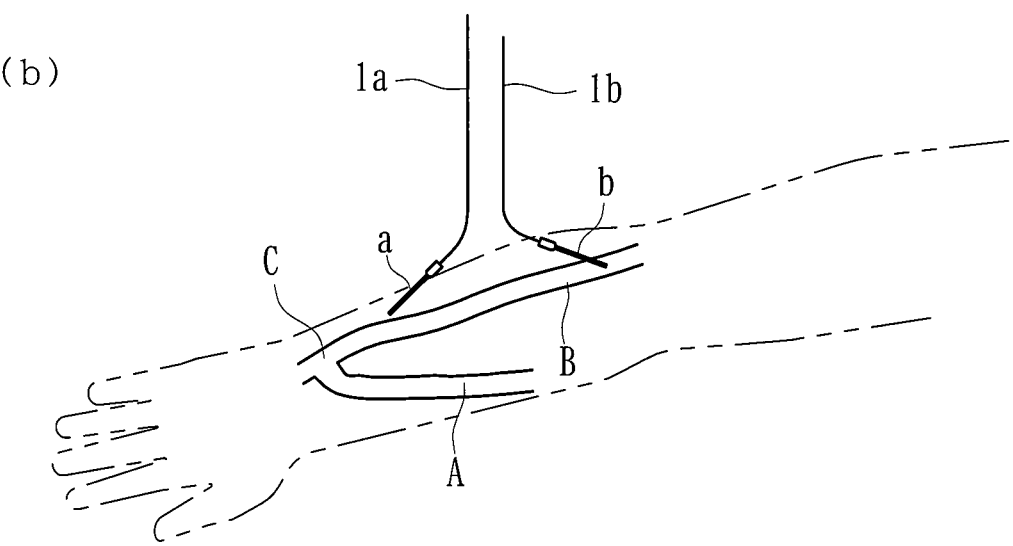

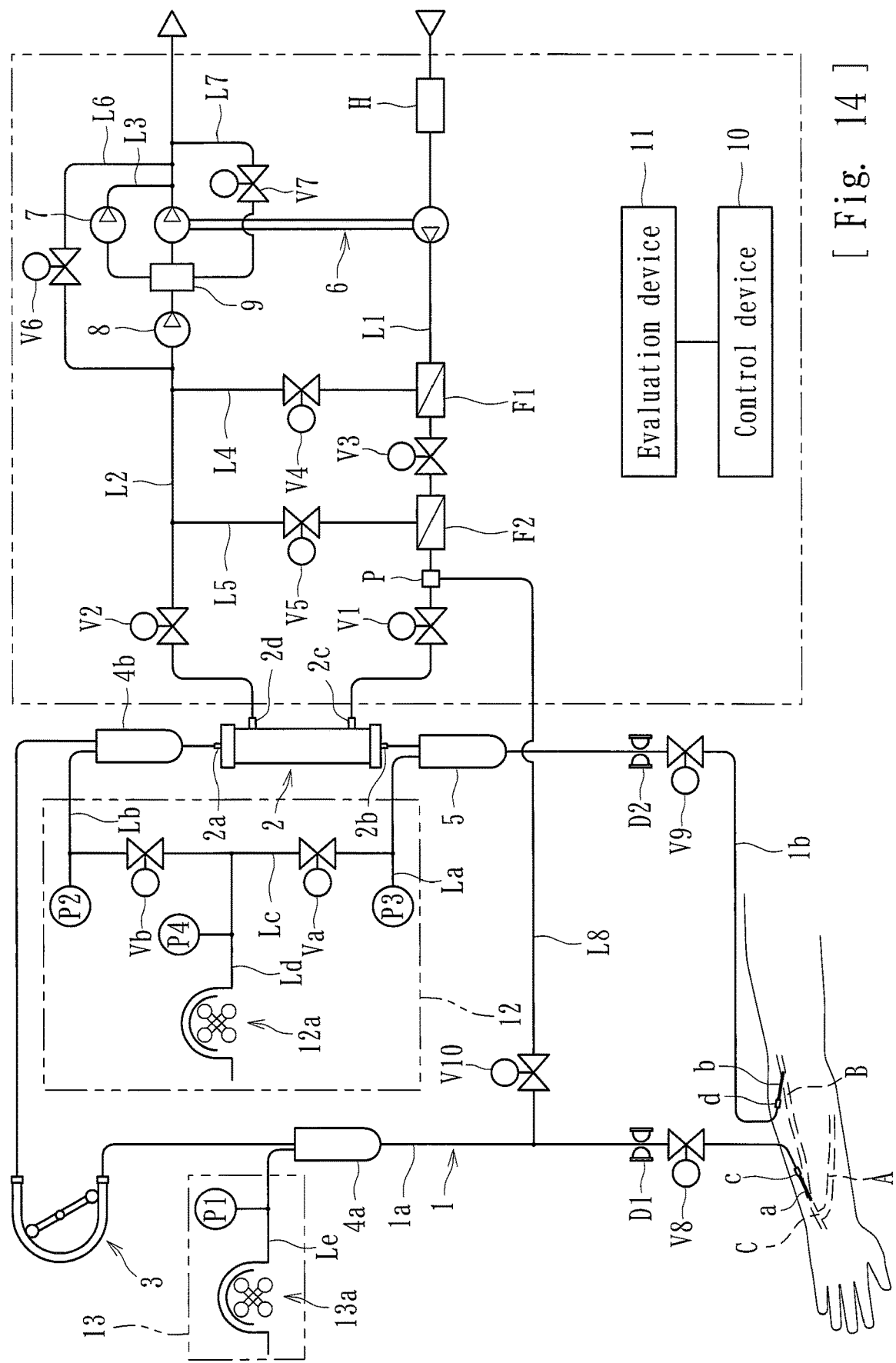
[ Fig. 14 ]

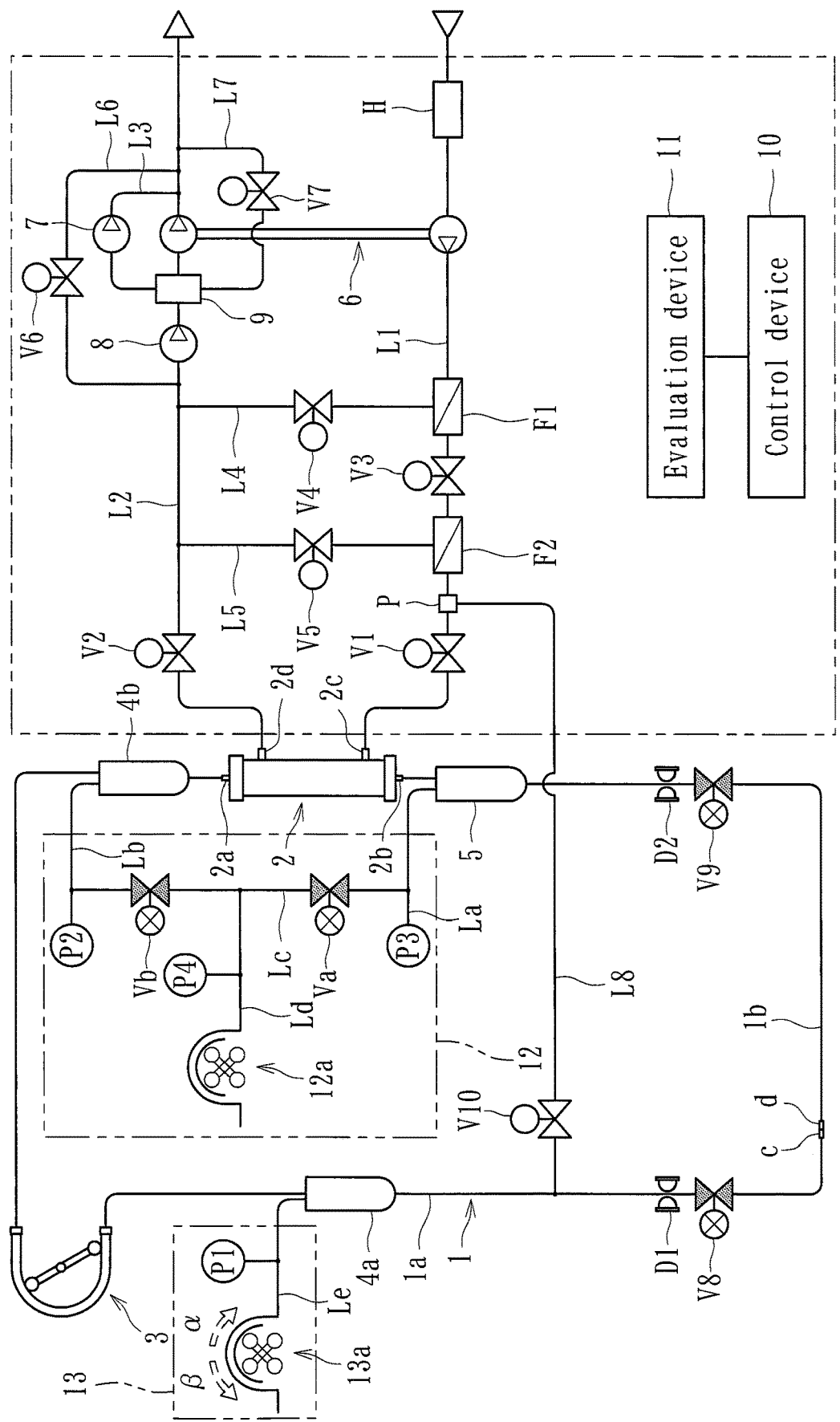
[Fig. 15]

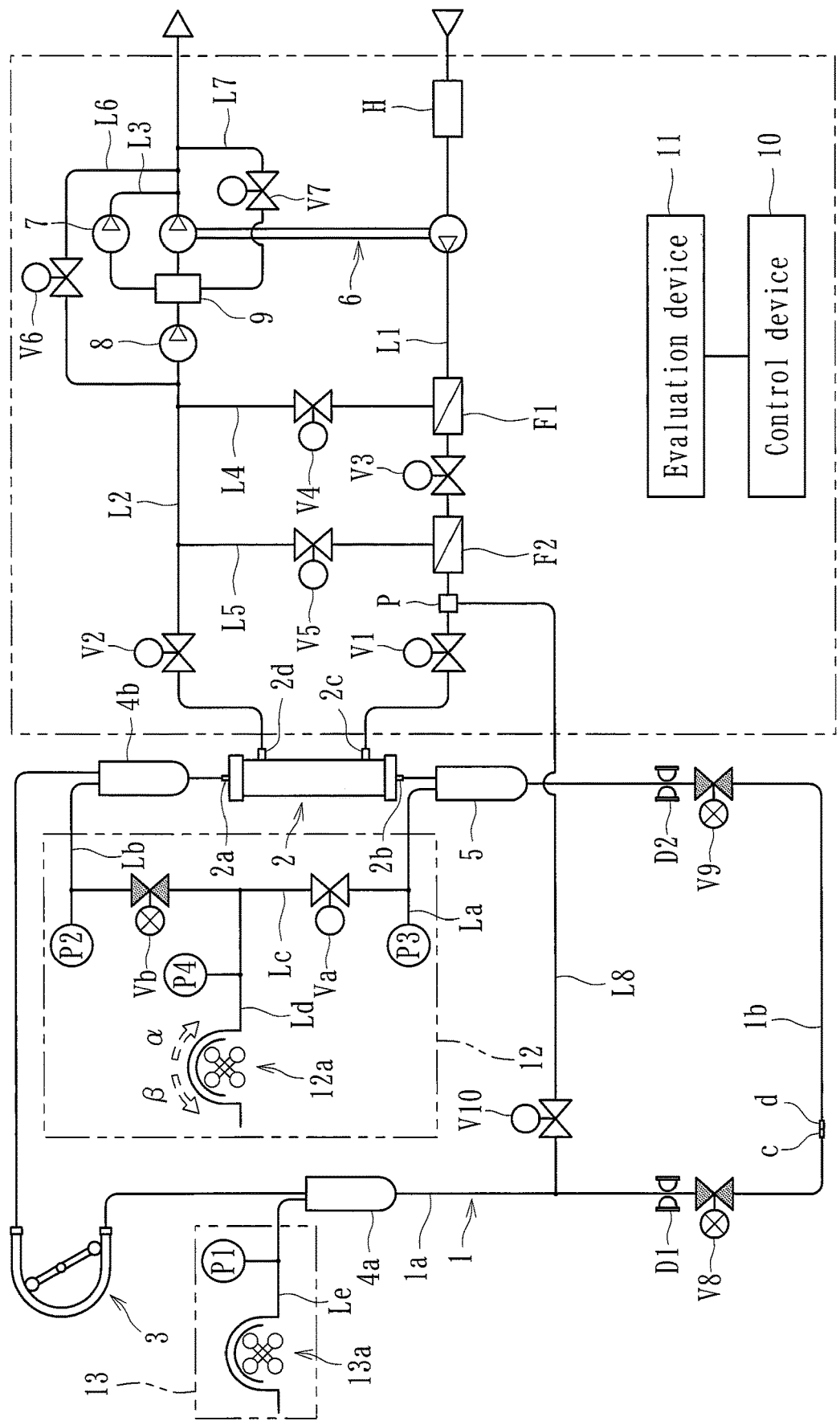
[Fig. 16]

[ Fig. 17 ]
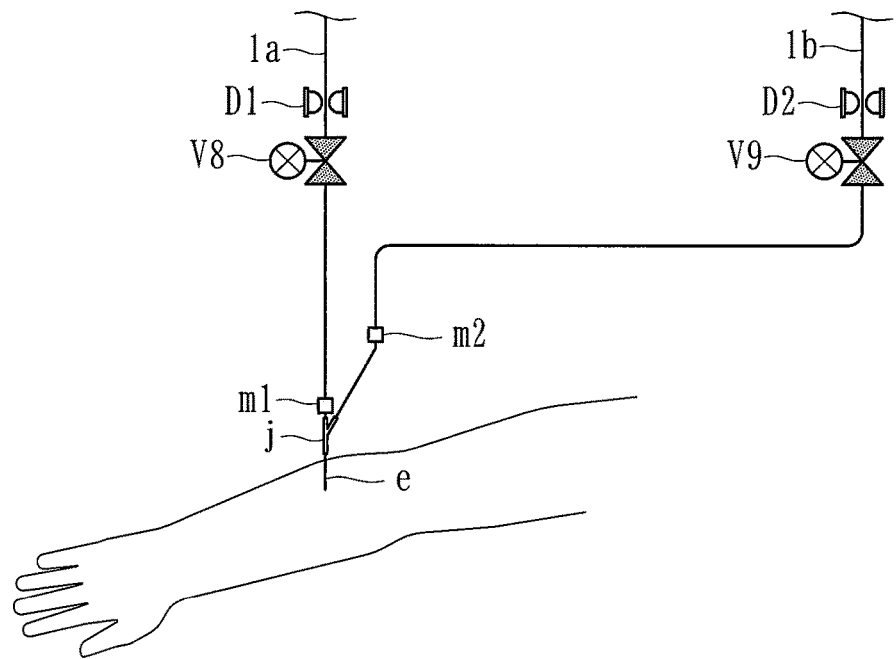
[ Fig. 18 ]
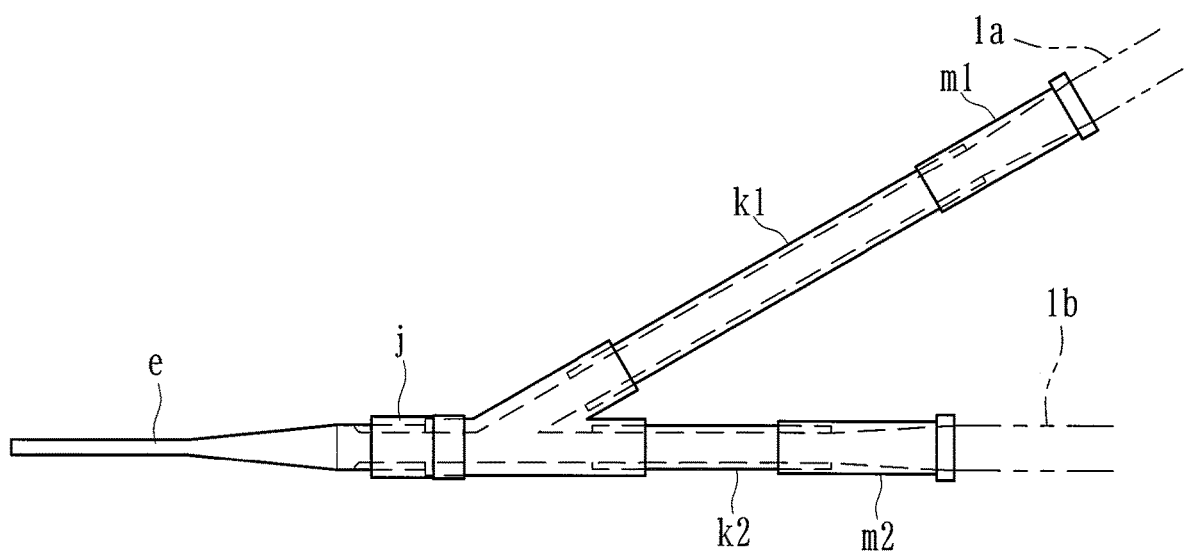

BLOOD PURIFICATION APPARATUS

FIELD

The present teachings relate to a blood purification apparatus capable of performing blood purification treatment with a blood purification device while extracorporeally circulating the blood of a patient through a blood circuit with a puncture needle being stuck in an access vessel of the patient.

BACKGROUND

In a general blood purification treatment such as dialysis treatment, a blood circuit formed of a flexible tube is used for extracorporeal circulation of the blood of a patient. The blood circuit includes an arterial blood circuit to the distal end of which an arterial puncture needle for collecting blood from the patient is attached, and a venous blood circuit to the distal end of which a venous puncture needle for returning the blood to the patient is attached. A dialyzer is provided between the arterial blood circuit and the venous blood circuit, and a blood pump is provided to the arterial blood circuit. Thus, the blood purification treatment is performable while the blood is extracorporeally circulated.

Prior to the blood purification treatment, the distal end of the arterial blood circuit and the distal end of the venous blood circuit with the arterial puncture needle and the venous puncture needle yet to be connected thereto are connected to each other, whereby a closed circuit is formed. Then, priming in which the closed circuit is filled with a priming solution is performed. To perform the blood purification treatment, the arterial puncture needle and the venous puncture needle are stuck into an access vessel of the patient, and the distal end of the arterial blood circuit and the distal end of the venous blood circuit that have undergone priming are connected to the arterial puncture needle and the venous puncture needle, respectively. Then, the blood pump is activated for blood removal. Such a technique has not been disclosed by any publicly known teaching, and there is no information on patent literature to be cited.

SUMMARY

In the above background art, however, it is difficult to evaluate from the appearance whether or not the arterial puncture needle and the venous puncture needle are appropriately stuck into the access vessel of the patient. Hence, if the blood pump is activated for blood purification treatment with the arterial puncture needle being stuck inappropriately, the extracorporeal circulation through the blood circuit cannot be performed appropriately. If the venous puncture needle is stuck inappropriately, the blood to be returned from the venous puncture needle during the extracorporeal circulation is not returned to the access vessel in a normal way. Such a problem also occurs in a blood purification apparatus employing a single-needle method in which an only puncture needle is connected to the distal ends of the respective blood circuits.

The present teachings have been conceived in view of the above circumstances and provides a blood purification apparatus capable of assuredly preventing the blood of a patient from being extracorporeally circulated through a blood circuit with a puncture needle being inappropriately stuck in an access vessel.

According to the teachings herein, there is provided a blood purification apparatus that includes a blood circuit to a distal end of which a puncture needle is connectable and through which blood of a patient extracorporeally circulate, and a blood purification device that purifies the blood flowing in the blood circuit. The blood purification apparatus is capable of performing blood purification treatment through the blood purification device while extracorporeally circulating the blood of the patient through the blood circuit with the puncture needle being stuck in an access vessel of the patient. The blood purification apparatus comprises a pressure-change-producing device capable of applying a positive pressure or a negative pressure to a distal portion of the blood circuit while the puncture needle is yet to be connected to the blood circuit, a pressure-change-detecting device capable of detecting a pressure change in the distal portion of the blood circuit that occurs when the distal portion of the blood circuit that is under the positive pressure or the negative pressure applied by the pressure-change-producing device is connected to the puncture needle that is stuck in the patient, and an evaluation device capable of evaluating a state of sticking of the puncture needle on the basis of the pressure change detected by the pressure-change-detecting device.

According to the teachings herein, in the blood purification apparatus taught herein, the distal portion of the blood circuit is provided with a clamping device that is capable of closing a flow route. Furthermore, the detection of the pressure change by the pressure-change-detecting device is performed by closing the clamping device so as to close the distal portion of the blood circuit, applying the positive pressure or the negative pressure to the distal portion from the pressure-change-producing device, and opening the clamping device with the puncture needle being connected to the distal end.

According to the teachings herein, in the blood purification apparatus taught herein, the pressure-change-producing device is a blood pump that is capable of delivering the blood of the patient through the blood circuit, and the positive pressure or the negative pressure is applied to the distal portion of the blood circuit when the blood pump is activated.

According to the teachings herein, in the blood purification apparatus taught herein, the pressure-change-producing device is a liquid-level-adjusting device that is capable of adjusting a level of a liquid surface in an air-trap chamber provided to the blood circuit by introducing or discharging air into or from the air-trap chamber, and the positive pressure or the negative pressure is applied to the distal portion of the blood circuit when the liquid-level-adjusting device is activated.

According to the teachings herein, in the blood purification apparatus according to the teachings herein, the pressure-change-producing device is an ultrafiltration pump for removing water from the blood flowing in the blood purification device, and the positive pressure or the negative pressure is applied to the distal portion of the blood circuit when the ultrafiltration pump is activated.

According to the teachings herein, in the blood purification apparatus according to the teachings herein, the pressure-change-detecting device is a pressure sensor that is capable of detecting a hydraulic pressure in the blood circuit.

According to the teachings herein, in the blood purification apparatus according to the teachings herein, the pressure-change-producing device is activated with the flow route provided by the blood circuit being filled with a priming solution after priming of the blood circuit is performed.

According to the teachings herein, the blood purification apparatus comprises the pressure-change-producing device capable of applying a positive pressure or a negative pressure to the distal portion of the blood circuit while the puncture needle is yet to be connected to the blood circuit, the pressure-change-detecting device capable of detecting a pressure change in the distal portion of the blood circuit that occurs when the distal portion of the blood circuit that is under the positive pressure or the negative pressure applied by the pressure-change-producing device is connected to the puncture needle that is stuck in the patient, and the evaluation device capable of evaluating a state of sticking of the puncture needle on the basis of the pressure change detected by the pressure-change-detecting device. Therefore, the blood of the patient can be assuredly prevented from being extracorporeally circulated through the blood circuit with the puncture needle being inappropriately stuck in the access vessel.

According to the teachings herein, the distal portion of the blood circuit is provided with the clamping device that is capable of closing the flow route. Furthermore, the detection of the pressure change by the pressure-change-detecting device is performed by closing the clamping device so as to close the distal portion of the blood circuit, applying the positive pressure or the negative pressure to the distal portion from the pressure-change-producing device, and opening the clamping device with the puncture needle being connected to the distal end. Therefore, the application of the positive pressure or the negative pressure by the pressure-change-producing device can be performed easily, and the detection of pressure change by the pressure-change-detecting device can be performed more accurately.

According to the teachings herein, the pressure-change-producing device is a blood pump that is capable of delivering the blood of the patient through the blood circuit, and the positive pressure or the negative pressure is applied to the distal portion of the blood circuit when the blood pump is activated. Therefore, with the use of the blood pump, the blood of the patient can be assuredly prevented from being extracorporeally circulated through the blood circuit with the puncture needle being inappropriately stuck in the access vessel.

According to the teachings herein, the pressure-change-producing device is a liquid-level-adjusting device that is capable of adjusting the level of the liquid surface in the air-trap chamber provided to the blood circuit by introducing or discharging air into or from the air-trap chamber, and the positive pressure or the negative pressure is applied to the distal portion of the blood circuit when the liquid-level-adjusting device is activated. Therefore, with the use of the liquid-level-adjusting device, the blood of the patient can be assuredly prevented from being extracorporeally circulated through the blood circuit with the puncture needle being inappropriately stuck in the access vessel.

According to the teachings herein, the pressure-change-producing device is an ultrafiltration pump for removing water from the blood flowing in the blood purification device, and the positive pressure or the negative pressure is applied to the distal portion of the blood circuit when the ultrafiltration pump is activated. Therefore, with the use of the ultrafiltration pump, the blood of the patient can be assuredly prevented from being extracorporeally circulated through the blood circuit with the puncture needle being inappropriately stuck in the access vessel.

According to the teachings herein, the pressure-change-detecting device is a pressure sensor that is capable of detecting a hydraulic pressure in the blood circuit. Therefore, with the use of the pressure sensor, the blood of the patient can be assuredly prevented from being extracorporeally circulated through the blood circuit with the puncture needle being inappropriately stuck in the access vessel.

According to the teachings herein, the pressure-change-producing device is activated with the flow route provided by the blood circuit being filled with a priming solution after priming of the blood circuit is performed. Therefore, in the transition from the priming to the blood removal, the evaluation of the state of sticking of the puncture needle into the access vessel can be performed appropriately. Accordingly, the blood of the patient can be assuredly prevented from being extracorporeally circulated through the blood circuit with the puncture needle being inappropriately stuck in the access vessel during the blood purification treatment.

BRIEF DESCRIPTION OF THE DRAWINGS

FIG. 1 is an overall diagram of a blood purification apparatus according to a first embodiment of the present teaching.

FIG. 2 is a schematic view illustrating a puncture needle and the distal end of a blood circuit (yet to be connected to each other) included in the blood purification apparatus.

FIG. 3 is a schematic view illustrating the puncture needle and the distal end of the blood circuit (connected to each other) included in the blood purification apparatus.

FIG. 4 is a diagram illustrating a state where a positive pressure and a negative pressure are generated by a pressure-change-producing device included in the blood purification apparatus.

FIG. 5 is a schematic view illustrating the distal ends of the blood circuits included in the blood purification apparatus that are yet to be connected to the respective puncture needles that are stuck in a patient.

FIG. 6 is another schematic view illustrating the distal ends of the blood circuits included in the blood purification apparatus that are yet to be connected to the respective puncture needles that are stuck in the patient.

FIG. 7 is a schematic view illustrating the distal ends of the blood circuits included in the blood purification apparatus that have been connected to the respective puncture needles that are stuck in the patient.

FIG. 8 is another schematic view illustrating the distal ends of the blood circuits included in the blood purification apparatus that have been connected to the respective puncture needles that are stuck in the patient.

FIG. 9 is a flow chart illustrating a control process performed in the blood purification apparatus.

FIG. 10 is a graph illustrating the pressure change detected by a pressure-change-detecting device included in the blood purification apparatus (when a positive pressure is generated by a pressure-change-producing device).

FIG. 11 is another graph illustrating the pressure change detected by the pressure-change-detecting device included in the blood purification apparatus (when a negative pressure is generated by the pressure-change-producing device).

FIG. 12 includes schematic views illustrating the distal ends of the blood circuits included in the blood purification apparatus that have been connected to the respective puncture needles that are stuck in the patient: part (a) illustrates a case where the sticking of the venous puncture needle is inappropriate (the needle has passed through an access vessel); and part (b) illustrates another case where the sticking of the venous puncture needle is inappropriate (the needle has not reached the access vessel).

FIG. 13 includes schematic views illustrating the distal ends of the blood circuits included in the blood purification apparatus that have been connected to the respective puncture needles that are stuck in the patient: part (a) illustrates a case where the sticking of the arterial puncture needle is inappropriate (the needle has passed through the access vessel); and part (b) illustrates another case where the sticking of the arterial puncture needle is inappropriate (the needle has not reached the access vessel).

FIG. 14 is an overall diagram of a blood purification apparatus according to a second embodiment of the present teaching.

FIG. 15 is a diagram illustrating a state where a positive pressure or a negative pressure is applied to a distal portion of an arterial blood circuit by a pressure-change-producing device included in the blood purification apparatus.

FIG. 16 is a diagram illustrating a state where a positive pressure or a negative pressure is applied to a distal portion of a venous blood circuit by the pressure-change-producing device included in the blood purification apparatus.

FIG. 17 is a diagram illustrating distal portions of respective blood circuits and a puncture needle (a single needle) included in a blood purification apparatus according to another embodiment of the present teaching.

FIG. 18 is a schematic view illustrating details of the puncture needle (the single needle).

DETAILED DESCRIPTION

Embodiments of the present teaching will now be described specifically with reference to the drawings.

A blood purification apparatus according to a first embodiment is a dialysis apparatus for giving a dialysis treatment and includes, as illustrated in FIG. 1, a blood circuit 1 including an arterial blood circuit 1a to the distal end of which an arterial puncture needle a is connectable and a venous blood circuit 1b to the distal end of which a venous puncture needle b is connectable, the blood circuit 1 being capable of allowing the blood of a patient to be extracorporeally circulated therethrough, a dialyzer 2 (a blood purification device) provided between the arterial blood circuit 1a and the venous blood circuit 1b and that purifies blood flowing in the blood circuit 1, a blood pump 3 provided to the arterial blood circuit 1a, a first arterial air-trap chamber 4a and a second arterial air-trap chamber 4b that are provided to the arterial blood circuit 1a, a venous air-trap chamber 5 provided to the venous blood circuit 1b, a dialysate introduction line L1 through which dialysate is introduced into the dialyzer 2, a dialysate drain line L2 through which drain liquid is discharged from the dialyzer 2, a control device 10, and an evaluation device 11.

The arterial blood circuit 1a is provided with a connector c at the distal end thereof, and the arterial puncture needle a is connectable to the distal end of the arterial blood circuit 1a with the connector c interposed therebetween. The blood pump 3, which is of a peristaltic type, the first arterial air-trap chamber 4a, and the second arterial air-trap chamber 4b are provided at respective halfway positions of the arterial blood circuit 1a. The arterial blood circuit 1a and the venous blood circuit 1b are provided at distal portions thereof with respective clamping devices (such as electromagnetic valves V8 and V9) that are capable of closing respective flow routes. The first arterial air-trap chamber 4a is provided between the distal end of the arterial blood circuit 1a and the position where the blood pump 3 is provided (i.e., on the upstream side with respect to the blood pump 3). The second arterial air-trap chamber 4b is provided between the position where the dialyzer 2 is provided and the position where the blood pump 3 is provided (i.e., on the downstream side with respect to the blood pump 3). The venous blood circuit 1b is provided with a connector d at the distal end thereof, and the venous puncture needle b is connectable to the distal end of the venous blood circuit 1b with the connector d interposed therebetween. The venous air-trap chamber 5 is provided at a halfway position of the venous blood circuit 1b.

The first arterial air-trap chamber 4a, the second arterial air-trap chamber 4b, and the venous air-trap chamber 5 are provided with respective pressure sensors (P1 to P3) that are each capable of detecting the pressure in an upper part (an air layer) thereof. The first arterial air-trap chamber 4a, the second arterial air-trap chamber 4b, and the venous air-trap chamber 5 are capable of detecting the pressures (hydraulic pressures) in a portion of the arterial blood circuit 1a that is on the upstream side with respect to the blood pump 3, in a portion of the arterial blood circuit 1a that is on the downstream side with respect to the blood pump 3, and in the venous blood circuit 1b, respectively. The pressure sensor P1 provided to the first arterial air-trap chamber 4a is capable of detecting the pressure for blood removal. The pressure sensor P2 provided to the second arterial air-trap chamber 4b is capable of detecting the pressure at the inlet of the dialyzer 2. The pressure sensor P3 provided to the venous air-trap chamber 5 is capable of detecting the venous pressure.

The arterial puncture needle a and the venous puncture needle (b) are connectable to the distal ends of the arterial blood circuit 1a and the venous blood circuit 1b, respectively. As illustrated in FIG. 2, the arterial puncture needle a and the venous puncture needle (b) are each a cannula (to be placed in a blood vessel) that is attached to a distal part (f) made of rigid resin or the like. The distal part (f) is connected to a joint (h), made of rigid resin or the like, with a forceps-held flexible tube (g) interposed therebetween. As illustrated in FIG. 2, the distal part (f), the forceps-held flexible tube (g), and the joint (h) are integrated into a single unit.

On the other hand, the arterial blood circuit 1a and the venous blood circuit 1b are each provided at the distal end thereof with a corresponding one of the connectors (joints c and d) made of rigid resin or the like. As illustrated in FIG. 3, the joint (c) or (d) fitted in the joint h provided to the puncture needle is screwed thereto with a lock ring R, whereby the joint (c) or (d) can be locked while being fitted therein. If the forceps-held flexible tube (g) is pinched by a pair of forceps, the flow route between the arterial puncture needle (a) or the venous puncture needle (b) and the arterial blood circuit 1a or the venous blood circuit 1b can be intercepted.

When the blood pump 3 is activated (to undergo normal rotation) in a state where the arterial puncture needle (a) connected to the distal end of the arterial blood circuit 1a and the venous puncture needle (b) connected to the venous blood circuit 1b are stuck in the patient, the blood of the patient flows through the arterial blood circuit 1a while undergoing bubble removal (while air bubbles contained therein are removed) in the first arterial air-trap chamber 4a and in the second arterial air-trap chamber 4b and reaches the dialyzer 2, where the blood is purified. Then, the blood undergoes bubble removal (air bubbles contained therein are removed) in the venous air-trap chamber 5, flows through the venous blood circuit 1b, and returns into the body of the patient. Thus, the blood of the patient can be purified by the dialyzer 2 while being extracorporeally circulated through the blood circuit 1 from the distal end of the arterial blood circuit 1a to the distal end of the venous blood circuit 1b.

The dialyzer 2 has, in a housing thereof, a blood inlet 2a (a blood introduction port), a blood outlet 2b (a blood delivery port), a dialysate inlet 2c (an inlet of the dialysate flow route, or a dialysate introduction port), and a dialysate outlet 2d (an outlet of the dialysate flow route, or a dialysate delivery port). The arterial blood circuit 1a is connected to the blood inlet 2a. The venous blood circuit 1b is connected to the blood outlet 2b. The dialysate inlet 2c and the dialysate outlet 2d are connected to the dialysate introduction line L1 and the dialysate drain line L2, respectively.

The dialyzer 2 houses a plurality of hollow fiber membranes (not illustrated), which serve as blood purification membranes for purifying the blood. The blood purification membranes in the dialyzer 2 define blood flow routes (each extending between the blood inlet 2a and the blood outlet 2b) in which the blood of the patient flows and dialysate flow routes (each extending between the dialysate inlet 2c and the dialysate outlet 2d) in which the dialysate flows. Typically, the blood flows on the inside of each of the hollow fibers, and the dialysate flows on the outside of the hollow fibers. The hollow fiber membranes serving as the blood purification membranes each have a number of very small holes (pores) extending therethrough from the outer peripheral surface to the inner peripheral surface. Hence, impurities and the like contained in the blood are allowed to penetrate through the membranes into the dialysate.

The arterial blood circuit 1a and the venous blood circuit 1b according to the first embodiment are further provided at the distal portions thereof with respective air-bubble detection devices (D1 and D2) capable of detecting gas (air bubbles) contained in the blood flowing in the arterial blood circuit 1a and the venous blood circuit 1b during the blood purification treatment. The air-bubble detection devices (D1 and D2) are each provided in a predetermined unit together with, for example, a blood-checking device, which is not illustrated, and the clamping device (V8 or V9).

The air-bubble detection devices (D1 and D2) are each a sensor capable of detecting air bubbles (air) flowing in a flexible tube that forms the arterial blood circuit 1a or the venous blood circuit 1b. The air-bubble detection devices (D1 and D2) each include, for example, an ultrasonic vibration element formed of a piezoelectric element, and an ultrasonic receiving element formed of a piezoelectric element. The air-bubble detection devices (D1 and D2) are each capable of emitting ultrasonic waves from the ultrasonic vibration element toward the flexible tube forming the arterial blood circuit 1a or the venous blood circuit 1b and is also capable of receiving the thus generated vibration by the ultrasonic receiving element.

The ultrasonic receiving element is configured such that the voltage changes with the vibration received. The ultrasonic receiving element is capable of detecting the flow of bubbles by the fact that the detected voltage has exceeded a predetermined threshold. Specifically, the ultrasonic attenuation factor of bubbles is higher than those of blood and substitution solutions. Hence, the ultrasonic waves transmitted through the liquid are detected. Then, if the detected voltage has exceeded the predetermined threshold, it is regarded that the flow of bubbles (gas) has been detected.

The dialysate introduction line L1 and the dialysate drain line L2 are provided with a duplex pump 6 that delivers a dialysate prepared to have a predetermined concentration to the dialyzer 2 and discharges waste products and the like (drain liquid) together with the dialysate from the dialyzer 2. Specifically, the duplex pump 6 is provided over the dialysate introduction line L1 and the dialysate drain line L2. When the duplex pump 6 is activated, the dialysate can be introduced into the dialyzer 2 through the dialysate introduction line L1, and the drain liquid can be discharged from the dialyzer 2 through the dialysate drain line L2.

The dialysate introduction line L1 is provided with electromagnetic valves V1 and V3 and filtration filters F1 and F2. The dialysate to be introduced into the dialyzer 2 can be filtered by the filtration filters F1 and F2, and the flow route of the dialysate is closable or openable at an arbitrary timing by the electromagnetic valves V1 and V3. The dialysate introduction line L1 is connected to the dialysate drain line L2 with bypass lines L4 and L5. The bypass lines L4 and L5 are provided with electromagnetic valves V4 and V5, respectively. Reference character H given in FIG. 1 denotes a heating device (a heater) for heating the dialysate to be supplied to the dialyzer 2 or to the blood circuit 1.

Furthermore, detour lines L3 and L6 for detouring the duplex pump 6 are connected to the dialysate drain line L2. The detour line L6 is provided with an electromagnetic valve V6. The detour line L3 is provided with an ultrafiltration pump 7. Hence, when the ultrafiltration pump 7 is activated in the process of extracorporeally circulating the blood of the patient through the blood circuit 1, ultrafiltration in which water is removed from the blood flowing through the dialyzer 2 can be performed.

Furthermore, the dialysate drain line L2 is provided with a pressurizing pump 8 at a position thereof on the upstream side (the left side in FIG. 1) with respect to the duplex pump 6. The pressurizing pump 8 adjusts the liquid pressure in the dialysate drain line L2 at the duplex pump 6. A release line L7 extends from a position of the dialysate drain line L2 between the pressurizing pump 8 and the duplex pump 6, with a degassing chamber 9 interposed therebetween. The dialysate drain line L2 and the release line L7 branching off therefrom are provided with electromagnetic valves V2 and V7, respectively. Hence, the flow route of the dialysate is closable or openable at an arbitrary timing.

A connection line L8 has one end thereof connected to a collecting port P (a sampling port) provided at a predetermined position of the dialysate introduction line L1 (in the first embodiment, between the electromagnetic valve V1 and the filtration filter F2) and the other end thereof connected to the arterial blood circuit 1a. The connection line L8 provides a flow route that allows the dialysate in the dialysate introduction line L1 to be supplied to the arterial blood circuit 1a. The connection line L8 is provided with an electromagnetic valve V10. When the electromagnetic valve V10 is opened, the dialysate in the dialysate introduction line L1 can be supplied to the blood circuit 1 (the arterial blood circuit 1a).

The control device 10 is a microcomputer electrically connected to various devices such as actuators and sensors included in the blood purification apparatus. The control device 10 is capable of controlling the following steps in the following order: a liquid-substituting step in which the pipes provided for the dialysate, such as the dialysate introduction line L1 and the dialysate drain line L2, are filled with the dialysate; a priming step in which the inside of the blood circuit 1 and the blood flow routes provided in the dialyzer 2 is substituted and filled with a priming solution (a physiological saline solution, the dialysate, or the like); a gas-purging step in which the dialysate flow routes provided in the dialyzer 2 are filled with the dialysate; a blood-removing step in which the blood of the patient is extracted into the blood circuit 1; a dialyzing step (a blood-purification-treatment step) in which the blood of the patient is purified by using the dialyzer 2 while the blood is extracorporeally circulated through the blood circuit 1; a blood-returning step in which the blood in the blood circuit 1 is returned to the patient; a draining step in which the liquid in the blood circuit 1 and/or the liquid in the dialyzer 2 are/is discharged to the dialysate drain line L2; a cleaning-and-disinfecting step in which the insides of the pipes included in the dialysis apparatus are cleaned and disinfected; and a presetting step in which the operation is withheld until the subsequent liquid-substituting step is performed.

The blood purification apparatus according to the first embodiment includes a pressure-change-producing device, a pressure-change-detecting device, and the evaluation device 11. The pressure-change-producing device is capable of applying a positive pressure and a negative pressure to the distal portions of the blood circuit 1 (the arterial blood circuit 1a and the venous blood circuit 1b) to which the arterial puncture needle a and the venous puncture needle b are yet to be connected. The pressure-change-producing device is, for example, the blood pump 3 (as described above, the blood pump 3 is capable of delivering the blood of the patient through the blood circuit).

Specifically, as illustrated in FIG. 4, the distal end of the arterial blood circuit 1a and the distal end of the venous blood circuit 1b are connected to each other (in a state where the arterial puncture needle (a) and the venous puncture needle (b) are yet to be connected thereto), whereby a closed circuit is provided. In this state, priming of the blood circuit 1 is performed. Subsequently, with the flow route provided by the blood circuit 1 being filled with the priming solution, the blood pump 3 (the pressure-change-producing device) is activated to undergo normal rotation (in the direction represented by the arrow illustrated in FIG. 4, or the direction of driving for the blood purification treatment). Note that, before the blood pump 3 is activated to undergo normal rotation, the clamping devices V8 and V9 are closed.

Thus, a negative pressure is applied to the distal portion of the arterial blood circuit 1a (specifically, a portion on the upstream side with respect to the blood pump 3 (between the clamping device V8 and the inlet of the blood pump 3)), whereas a positive pressure is applied to the distal portion of the venous blood circuit 1b (specifically, a portion on the downstream side with respect to the blood pump 3 (between the clamping device V9 and the outlet of the blood pump 3)). As described above, the pressure-change-producing device according to the first embodiment corresponds to the blood pump 3 capable of delivering the blood of the patient through the blood circuit 1, and is capable of applying a positive pressure and a negative pressure to the distal portions of the blood circuit 1 by activating the blood pump 3.

In the first embodiment, the blood pump 3 (the pressure-change-producing device) is activated to undergo normal rotation (in the direction represented by the arrow illustrated in FIG. 4, or the direction of driving for the blood purification treatment), whereby a negative pressure is applied to the distal portion of the arterial blood circuit 1a while a positive pressure is applied to the distal portion of the venous blood circuit 1b. Alternatively, the blood pump 3 (the pressure-change-producing device) may be activated to undergo reverse rotation (in the direction opposite to the direction of driving for the blood purification treatment) so that a positive pressure is applied to the distal portion of the arterial blood circuit 1a while a negative pressure is applied to the distal portion of the venous blood circuit 1b.

Apart from the above work of applying a negative pressure and a positive pressure to the distal portions of the arterial blood circuit 1a and the venous blood circuit 1b, as illustrated in FIGS. 5 and 6, the arterial puncture needle a is stuck into an upstream portion of an access vessel (a position near a shunt part C where an artery A and a vein B meet), and the venous puncture needle (b) is stuck into a downstream portion of the access vessel (a position of the vein B on the downstream side with respect to the position near the shunt part C). The sticking of the arterial puncture needle (a) and the venous puncture needle b into the patient is performed manually by a medical staff.

The pressure-change-detecting device is capable of detecting the pressure change that occurs at the distal portions of the blood circuit 1 (including the arterial blood circuit 1a and the venous blood circuit 1b) when the distal portions that are under the positive pressure and the negative pressure generated by the pressure-change-producing device are connected to the puncture needles (the arterial puncture needle a and the venous puncture needle b) that are stuck in the patient. In the first embodiment, the pressure-change-detecting device includes the pressure sensors (P1 to P3) capable of detecting the pressures in the air layers of the respective air-trap chambers provided to the blood circuit 1.

Specifically, as illustrated in FIGS. 7 and 8, the distal end of the venous blood circuit 1b is connected to the venous puncture needle (b) that is stuck in the access vessel (the joint (h) for the puncture needle is fitted onto the joint (d) as illustrated in FIG. 3 and is screwed thereon with the lock ring R so that the fitted state is locked). Subsequently, the clamping device V9 is opened. Then, as graphed in FIG. 10, a pressure ($\beta$) detected by the pressure sensor P3 (or the pressure sensor P2) serving as a pressure-change-detecting device drops to a level below a threshold ($\alpha$) while a predetermined period of time (for example, about 1 (s)) elapses. More specifically, a positive pressure is applied to the distal portion of the venous blood circuit 1b in advance by the pressure-change-producing device. Hence, when the clamping device V9 is opened, the positive pressure is removed if the state of sticking of the venous puncture needle (b) is appropriate. Therefore, the pressure ($\beta$) detected by the pressure sensor P3 (or the pressure sensor P2) drops to a level below the threshold ($\alpha$) while a predetermine period of time elapses.

Furthermore, as illustrated in FIGS. 7 and 8, the distal end of the arterial blood circuit 1a is connected to the arterial puncture needle a that is stuck in the access vessel (the joint (h) for the puncture needle is fitted onto the joint (c) as illustrated in FIG. 3 and is screwed thereon with the lock ring R so that the fitted state is locked). Subsequently, the clamping device V8 is opened. Then, as graphed in FIG. 11, a pressure ($\gamma$) detected by the pressure sensor P1 serving as a pressure-change-detecting device rises to a level above the threshold ($\alpha$) while a predetermined period of time (for example, about 1 (s)) elapses. More specifically, a negative pressure is applied to the distal portion of the arterial blood circuit 1a in advance by the pressure-change-producing device. Hence, when the clamping device V8 is opened, the negative pressure is removed if the state of sticking of the arterial puncture needle a is appropriate. Therefore, the pressure ($\gamma$) detected by the pressure sensor P1 rises to a level above the threshold ($\alpha$) while a predetermine period of time elapses.

The evaluation device 11 is a microcomputer or the like that is electrically connected to relevant devices such as the control device 10 and the pressure-change-detecting devices. The evaluation device 11 is capable of evaluating the state of sticking of the puncture needles (the arterial puncture needle (a) and the venous puncture needle (b)) on the basis of the pressure changes detected by the respective pressure-change-detecting devices (in the first embodiment, the pressure sensors (P1 to P3)). Specifically, if the pressure changes detected by the respective pressure-change-detecting devices each show a corresponding one of the tendencies that are graphed in FIGS. 10 and 11 (such as a tendency that the pressure drops to a level below the threshold ($\alpha$) and a tendency that the pressure rises to a level above the threshold ($\alpha$) in a predetermined period of time), the state of sticking of the puncture needles (the arterial puncture needle (a) and the venous puncture needle (b)) is evaluated to be appropriate. If the pressure changes do not show the above tendencies, the state of sticking of the puncture needles (the arterial puncture needle (a) and the venous puncture needle (b)) is evaluated to be inappropriate.

For example, as illustrated in FIG. 12, suppose that the state of sticking of the venous puncture needle (b) is inappropriate with the venous puncture needle (b) having passed through the vein B serving as the access vessel (see part (a) of FIG. 12) or with the venous puncture needle (b) not reaching the vein B (see part (b) of FIG. 12). When the clamping device V9 is opened in such a state, the pressure ($\beta$) detected by the pressure sensor P3 (or the pressure sensor P2) serving as the pressure-change-detecting device does not show the tendency illustrated in FIG. 10 (the pressure drops to a level below the threshold ($\alpha$) in a predetermined period of time). Hence, such a state of sticking of the venous puncture needle (b) is evaluated to be inappropriate.

Likewise, as illustrated in FIG. 13, suppose that the state of sticking of the arterial puncture needle (a) is inappropriate with the arterial puncture needle (a) having passed through the vein B serving as the access vessel near the shunt part C (see part (a) of FIG. 13) or with the arterial puncture needle (a) not reaching the vein B (see part (b) of FIG. 13). When the clamping device V8 is opened in such a state, the pressure ($\gamma$) detected by the pressure sensor P1 serving as the pressure-change-detecting device does not show the tendency illustrated in FIG. 11 (the pressure rises to a level above the threshold ($\alpha$) in a predetermined period of time). Hence, such a state of sticking of the arterial puncture needle a is evaluated to be inappropriate.

The evaluation device 11 evaluates the state of sticking of each of the puncture needles (the arterial puncture needle (a) and the venous puncture needle (b)) by detecting whether the value detected by a corresponding one of the pressure-change-detecting devices has dropped or risen to a level below or above the threshold ($\alpha$) in a predetermined period of time. Alternatively, for example, the evaluation device 11 may evaluate the state of sticking of each of the puncture needles only on the basis of pressure change (such as the rate of pressure change or the speed of pressure change), not with reference to the threshold ($\alpha$). As another alternative, data on pressure changes that is taken for each patient may be stored, and the evaluation device 11 may evaluate the state of sticking of each of the puncture needles by checking whether or not the detected changes conform to the stored data.

Now, a control process of evaluating the state of sticking that is performed in the blood purification apparatus according to the first embodiment will be described with reference to the flow chart illustrated in FIG. 9.

After the priming of the blood circuit 1 is performed, the flow route provided by the blood circuit 1 is filled with the priming solution (with the distal end of the arterial blood circuit 1a and the distal end of the venous blood circuit 1b connected to each other as illustrated in FIG. 4). In this state, while the clamping devices V8 and V9 are closed, the blood pump 3 is activated (to undergo normal rotation) (S1). Thus, a negative pressure is applied to the distal portion of the arterial blood circuit 1a, whereas a positive pressure is applied to the distal portion of the venous blood circuit 1b.

Subsequently, in step S2, the distal end of the arterial blood circuit 1a and the distal end of the venous blood circuit 1b are connected to the arterial puncture needle (a) and the venous puncture needle (b), respectively, that are stuck in the access vessel of the patient. Then, in step S3, the clamping devices V8 and V9 are opened. Thus, the distal portion of the arterial blood circuit 1a and the distal portion of the venous blood circuit 1b are released from the negative pressure and the positive pressure, whereby predetermined pressure changes occur therein. Then, the evaluation device 11 checks whether or not the pressure changes detected by the respective pressure-change-detecting devices (the pressure sensors (P1 to P3)) show the respective predetermined tendencies (S4). If the detected pressure changes show the predetermined tendencies, the process proceeds to step S5, where the state of sticking is determined to be normal (or appropriate).

If either of the pressure changes detected by the pressure-change-detecting devices (the pressure sensors (P1 to P3)) does not show a corresponding one of the predetermined tendencies, the process proceeds to step S6, where the state of sticking is determined to be abnormal (or inappropriate). If the state of sticking is determined to be abnormal, it is preferable to notify the inappropriate state of sticking of the arterial puncture needle (a) or the venous puncture needle (b) through a specific notifying device (for example, a display such as a monitor, a warning lamp, a speaker, or the like).

The first embodiment employs the pressure-change-producing device capable of applying a positive pressure or a negative pressure to the distal portions of the blood circuit 1 that are yet to be connected to the puncture needles (the arterial puncture needle (a) and the venous puncture needle (b)), the pressure-change-detecting devices capable of detecting pressure changes in the distal portions of the blood circuit 1 that occur when the distal portions of the blood circuit 1 to which the positive pressure or the negative pressure is applied by the pressure-change-producing device are connected to the puncture needles (the arterial puncture needle a and the venous puncture needle (b)) that are stuck in the patient, and the evaluation device 11 capable of evaluating the state of sticking of the puncture needles (the arterial puncture needle (a) and the venous puncture needle (b)) on the basis of the pressure changes detected by the pressure-change-detecting devices. Therefore, the blood of the patient can be assuredly prevented from being extracorporeally circulated through the blood circuit 1 with the puncture needles being inappropriately stuck in the access vessel.

Furthermore, the distal portions of the blood circuit 1 are provided with the clamping devices (V8 and V9), respectively, that are capable of closing the flow route. With the clamping devices (V8 and V9) being closed so that the distal portions of the blood circuit 1 are closed, a positive pressure or a negative pressure is applied to the distal portions by the pressure-change-producing device. Then, with the puncture needles (the arterial puncture needle (a) and the venous puncture needle (b)) being connected, the clamping devices (V8 and V9) are opened, and changes in the pressure are detected by the pressure-change-detecting devices. Therefore, the application of the positive pressure or the negative pressure by the pressure-change-producing device can be performed easily, and the detection of pressure changes by the pressure-change-detecting devices can be performed more accurately.

Furthermore, the pressure-change-producing device is the blood pump 3 capable of delivering the blood of the patient through the blood circuit 1, and a positive pressure or a negative pressure is applied to the distal portions of the blood circuit 1 with the activation of the blood pump 3. Therefore, with the use of the blood pump 3, the blood of the patient can be assuredly prevented from being extracorporeally circulated through the blood circuit 1 with the puncture needles (the arterial puncture needle (a) and the venous puncture needle (b)) being inappropriately stuck in the access vessel. Furthermore, the pressure-change-detecting device includes the pressure sensors (P1 to P3) each being capable of detecting the hydraulic pressure in the blood circuit 1. Therefore, with the use of the pressure sensors (P1 to P3), the blood of the patient can be assuredly prevented from being extracorporeally circulated through the blood circuit 1 with the puncture needles being inappropriately stuck in the access vessel. While the first embodiment concerns a case where the pressure-change-detecting device includes the pressure sensors (P1 to P3) capable of detecting the pressures in the air layers formed in the respective air-trap chambers provided to the blood circuit 1, the pressure-change-detecting device may be capable of detecting the hydraulic pressure in the blood circuit 1, instead of being provided to the air-trap chambers.

Furthermore, after the priming of the blood circuit 1 is performed, the pressure-change-producing device is activated with the flow route provided by the blood circuit 1 being filled with the priming solution. Therefore, in the transition from the priming to the blood removal, the evaluation of the state of sticking of the puncture needles (the arterial puncture needle (a) and the venous puncture needle (b)) into the access vessel can be performed appropriately. Accordingly, the blood of the patient can be assuredly prevented from being extracorporeally circulated through the blood circuit 1 with the puncture needle being inappropriately stuck in the access vessel during the blood purification treatment. The evaluation of the state of sticking of the puncture needles (the arterial puncture needle (a) and the venous puncture needle (b)) that is performed by the evaluation device 11 may be performed in any other step that is performed before the blood of the patient is extracorporeally circulated through the blood circuit 1.

Now, a blood purification apparatus according to a second embodiment of the present teaching will be described.

As with the case of the first embodiment, the blood purification apparatus according to the second embodiment is a dialysis apparatus for giving a dialysis treatment and includes, as illustrated in FIG. 14, a blood circuit 1 including an arterial blood circuit 1a to the distal end of which an arterial puncture needle (a) is connectable and a venous blood circuit 1b to the distal end of which a venous puncture needle (b) is connectable, the blood circuit 1 being capable of allowing the blood of a patient to be extracorporeally circulated therethrough, a dialyzer 2 (a blood purification device) provided between the arterial blood circuit 1a and the venous blood circuit 1b and that purifies blood flowing in the blood circuit 1, a blood pump 3 provided to the arterial blood circuit 1a, a first arterial air-trap chamber 4a and a second arterial air-trap chamber 4b that are provided to the arterial blood circuit 1a, a venous air-trap chamber 5 provided to the venous blood circuit 1b, a dialysate introduction line L1 through which dialysate is introduced into the dialyzer 2, a dialysate drain line L2 through which drain liquid is discharged from the dialyzer 2, a control device 10, an evaluation device 11, and liquid-level-adjusting devices 12 and 13. Elements that are the same as those described in the first embodiment are denoted by corresponding ones of the reference numerals, and detailed description of those elements is omitted.

The pressure-change-producing device according to the second embodiment includes the liquid-level-adjusting devices (12 and 13) each being capable of adjusting the level of the liquid surface by introducing or discharging air into or from a corresponding one of the air-trap chambers (the first arterial air-trap chamber 4a, the second arterial air-trap chamber 4b, and the venous air-trap chamber 5) provided to the blood circuit 1. When the liquid-level-adjusting devices (12 and 13) are activated, a positive pressure or a negative pressure is applied to the distal portions of the blood circuit 1.

Specifically, the liquid-level-adjusting device 12 includes an extension tube La extending from an upper part (the air layer) of the venous air-trap chamber 5, an extension tube Lb extending from the upper part (the air layer) of the second arterial air-trap chamber 4b, a connecting tube Lc connected to the extension tubes La and Lb, a release tube Ld having one end thereof connected to the connecting tube Lc and the other end thereof being open to the atmosphere, and a liquid-level-adjusting pump 12a provided to the release tube Ld. The connecting tube Lc is provided with an electromagnetic valve Va that opens and closes a portion thereof on the side of the extension tube La and an electromagnetic valve Vb that opens and closes a portion thereof on the side of the extension tube Lb.

The liquid-level-adjusting pump 12a is a peristaltic pump capable of undergoing normal rotation (the rotation in a direction ($\alpha$) indicated in FIG. 16) and reverse rotation (the rotation in a direction ($\beta$) indicated in FIG. 16). The release tube Ld is squeezed in the long-side direction thereof, whereby air can be introduced into or discharged from the upper part of the venous air-trap chamber 5 or the second arterial air-trap chamber 4b as intended. When the liquid-level-adjusting pump 12a is activated to undergo normal rotation, air is taken from the distal end of the release tube Ld. Therefore, when the electromagnetic valve Va is open, the air is introduced into the venous air-trap chamber 5 through the extension tube La, whereby the level of the liquid surface can be lowered. When the liquid-level-adjusting pump 12a is activated to undergo reverse rotation, the air is discharged from the distal end of the release tube Ld. Therefore, when the electromagnetic valve Va is open, the air is discharged from the venous air-trap chamber 5 through the extension tube La, whereby the level of the liquid surface can be raised.

Likewise, when the liquid-level-adjusting pump 12a is activated to undergo normal rotation, air is taken from the distal end of the release tube Ld. Therefore, when the electromagnetic valve Vb is open, the air is introduced into the second arterial air-trap chamber 4b through the extension tube Lb, whereby the level of the liquid surface can be lowered. When the liquid-level-adjusting pump 12a is activated to undergo reverse rotation, the air is discharged from the distal end of the release tube Ld. Therefore, when the electromagnetic valve Vb is open, the air is discharged from the second arterial air-trap chamber 4b through the extension tube Lb, whereby the level of the liquid surface can be raised.

In the second embodiment, as illustrated in FIG. 16, after the priming of the blood circuit 1 is performed, the flow route provided by the blood circuit 1 is filled with the priming solution (with the distal end of the arterial blood circuit 1a and the distal end of the venous blood circuit 1b connected to each other as illustrated in FIG. 16). In this state, while the clamping devices V8 and V9 are closed (with at least one of the electromagnetic valves Va and Vb being open), the liquid-level-adjusting pump 12a of the liquid-level-adjusting device 12 is activated to undergo normal rotation. Thus, a positive pressure can be applied to the distal portion of the venous blood circuit 1b. If the liquid-level-adjusting pump 12a of the liquid-level-adjusting device 12 is activated to undergo reverse rotation, a negative pressure can be applied to the distal portion of the venous blood circuit 1b.

The liquid-level-adjusting device 13 includes a release tube Le extending from an upper part (the air layer) of the first arterial air-trap chamber 4a and having the other end thereof being open to the atmosphere, and a liquid-level-adjusting pump 13a provided to the release tube Le. The liquid-level-adjusting pump 13a is a peristaltic pump capable of undergoing normal rotation (the rotation in the direction ($\alpha$) indicated in FIG. 15) and reverse rotation (the rotation in the direction $\beta$ indicated in FIG. 15). The release tube Le is squeezed in the long-side direction thereof, whereby air can be introduced into or discharged from the upper part of the first arterial air-trap chamber 4a as intended.

When the liquid-level-adjusting pump 13a is activated to undergo normal rotation, air is taken from the distal end of the release tube Le. Therefore, the air is introduced into the first arterial air-trap chamber 4a, whereby the level of the liquid surface can be lowered. When the liquid-level-adjusting pump 13a is activated to undergo reverse rotation, the air is discharged from the distal end of the release tube Le. Therefore, the air is discharged from the first arterial air-trap chamber 4a, whereby the level of the liquid surface can be raised.

In the second embodiment, as illustrated in FIG. 15, after the priming of the blood circuit 1 is performed, the flow route provided by the blood circuit 1 is filled with the priming solution (with the distal end of the arterial blood circuit 1a and the distal end of the venous blood circuit 1b connected to each other as illustrated in FIG. 15). In this state, while the clamping devices V8 and V9 are closed, the liquid-level-adjusting pump 13a of the liquid-level-adjusting device 13 is activated to undergo normal rotation. Thus, a positive pressure can be applied to the distal portion of the arterial blood circuit 1a. If the liquid-level-adjusting pump 13a of the liquid-level-adjusting device 13 is activated to undergo reverse rotation, a negative pressure can be applied to the distal portion of the arterial blood circuit 1a.

To summarize, after the priming of the blood circuit 1 is performed, the flow route provided by the blood circuit 1 is filled with the priming solution (with the distal end of the arterial blood circuit 1a and the distal end of the venous blood circuit 1b connected to each other). In this state, while the clamping devices V8 and V9 are closed, a negative pressure or a positive pressure is applied to the distal portions of the arterial blood circuit 1a and the venous blood circuit 1b. Then, with the puncture needles (the arterial puncture needle (a) and the venous puncture needle (b)) being connected, the clamping devices (V8 and V9) are opened. Thus, pressure changes can be detected by the pressure-change-detecting devices, and the state of sticking of the puncture needles (the arterial puncture needle (a) and the venous puncture needle (b)) can be evaluated by the evaluation device 11 on the basis of the pressure changes detected by the pressure-change-detecting devices.

The second embodiment employs the pressure-change-producing device capable of applying a positive pressure or a negative pressure to the distal portions of the blood circuit 1 that are yet to be connected to the puncture needles (the arterial puncture needle (a) and the venous puncture needle (b)), the pressure-change-detecting devices capable of detecting pressure changes in the distal portions of the blood circuit 1 that occur when the distal portions of the blood circuit 1 to which the positive pressure or the negative pressure is applied by the pressure-change-producing device are connected to the puncture needles (the arterial puncture needle (a) and the venous puncture needle (b)) that are stuck in the patient, and the evaluation device 11 capable of evaluating the state of sticking of the puncture needles (the arterial puncture needle (a) and the venous puncture needle (b)) on the basis of the pressure changes detected by the pressure-change-detecting devices. Therefore, the blood of the patient can be assuredly prevented from being extracorporeally circulated through the blood circuit 1 with the puncture needles being inappropriately stuck in the access vessel.

Furthermore, the distal portions of the blood circuit 1 are provided with the clamping devices (V8 and V9), respectively, that are capable of closing the flow route. With the clamping devices (V8 and V9) being closed so that the distal portions of the blood circuit 1 are closed, a positive pressure or a negative pressure is applied to the distal portions by the pressure-change-producing device. Then, with the puncture needles (the arterial puncture needle (a) and the venous puncture needle (b)) being connected, the clamping devices (V8 and V9) are opened, and changes in the pressure are detected by the respective pressure-change-detecting devices. Therefore, the application of the positive pressure or the negative pressure by the pressure-change-producing device can be performed easily, and the detection of pressure changes by the pressure-change-detecting devices can be performed more accurately.

Furthermore, the pressure-change-producing device according to the second embodiment includes the liquid-level-adjusting devices (12 and 13) capable of adjusting the levels of the liquid surfaces in the respective air-trap chambers provided to the blood circuit 1 by introducing or discharging air into or from the air-trap chambers. When the liquid-level-adjusting devices (12 and 13) are activated, a positive pressure or a negative pressure is applied to the distal portions of the blood circuit 1. Therefore, with the use of the liquid-level-adjusting devices (12 and 13), the blood of the patient can be assuredly prevented from being extracorporeally circulated through the blood circuit 1 with the puncture needles (the arterial puncture needle (a) and the venous puncture needle (b)) being inappropriately stuck in the access vessel.

While the first and second embodiments have been described above, the present teaching is not limited thereto. For example, as illustrated in FIGS. 17 and 18, the blood purification apparatus may include an only puncture needle (e) (a single needle) connected to each of the distal ends of the arterial blood circuit 1a and the venous blood circuit 1b with a wye (j) interposed therebetween (e.g., a branch structure joining together with a "Y" shape). Thus, with the puncture needle (e) being stuck in the access vessel of the patient, the blood of the patient may be extracorporeally circulated. The other end of the wye (j) branches into two, as illustrated in FIG. 18. The two ends are connected to flexible tubes k1 and k2, respectively. The flexible tube k1 is provided with a connector m1 to which the distal end of the arterial blood circuit 1a is connected. The flexible tube k2 is provided with a connector m2 to which the distal end of the venous blood circuit 1*b* is connected. The connectors m1 and m2 according to such an embodiment are each provided with a Luer taper and a screw. The Luer taper is connectable to the distal end of a corresponding one of the arterial blood circuit 1*a* and the venous blood circuit 1*b*. Hence, the connectors m1 and m2 are lockable to the distal ends.

After the priming of the blood circuit 1 is performed, the flow route provided by the blood circuit 1 is filled with the priming solution (with the distal end of the arterial blood circuit 1*a* and the distal end of the venous blood circuit 1*b* connected to each other). In this state, while the clamping devices V8 and V9 are closed, a negative pressure or a positive pressure is applied to the distal portion of the arterial blood circuit 1*a* or the venous blood circuit 1*b*. Then, with the puncture needle (e) (the single needle) being connected, the clamping devices (V8 and V9) are opened as illustrated in FIG. 17. Thus, pressure changes can be detected by the pressure-change-detecting devices, and the state of sticking of the puncture needle (e) can be evaluated by the evaluation device 11 on the basis of the pressure changes detected by the pressure-change-detecting devices.

The pressure-change-producing device according to each of the above embodiments includes either the blood pump 3 (the first embodiment) capable of delivering the blood of the patient through the blood circuit 1 or the liquid-level-adjusting devices (12 and 13) (the second embodiment) capable of adjusting the level of the liquid surfaces in the respective air-trap chambers provided to the blood circuit 1 by introducing or discharging air into or from the air-trap chambers. Alternatively, for example, the pressure-change-producing device may be the ultrafiltration pump 7 for removing water from the blood flowing in the dialyzer 2 (a blood purification device). With the activation of the ultrafiltration pump 7, a positive pressure or a negative pressure may be applied to the distal portions of the blood circuit 1. In that case, with the use of the ultrafiltration pump 7, the blood of the patient can be assuredly prevented from being extracorporeally circulated through the blood circuit 1 with the puncture needles (the arterial puncture needle (a) and the venous puncture needle (b), or the only puncture needle e) being inappropriately stuck in the access vessel.

The pressure-change-producing device and the pressure-change-detecting device are not limited to those described in the above embodiments and may be any other devices that are intended for blood purification treatment or devices that are additionally provided. While the above embodiments each concerns a dialysis apparatus intended for dialysis treatment, the present teaching is also applicable to any other blood purification apparatus capable of purifying the blood of a patient while extracorporeally circulating the blood (for example, any of a blood purification apparatus, a blood-plasma-absorbing apparatus, and the like that are used in a hemodiafiltration method, a hemofiltration method, and acetate-free biofiltration (AFBF)).

The present teaching is applicable to any blood purification apparatus having a different appearance, another function, or the like, as long as the apparatus includes a pressure-change-producing device capable of applying a positive pressure or a negative pressure to the distal ends of a blood circuit to which puncture needles are yet to be connected, a pressure-change-detecting device capable of detecting pressure changes in the distal portions of the blood circuit that occur when the distal portions that are each under the positive pressure or the negative pressure applied by the pressure-change-producing device are connected to the puncture needles that are stuck in a patient, and an evaluation device capable of evaluating the state of sticking of the puncture needles on the basis of the pressure changes detected by the pressure-change-detecting device.

REFERENCE SIGN LIST 1 blood circuit
1*a* arterial blood circuit
1*b* venous blood circuit
2 dialyzer (blood purification device)
3 blood pump
4*a* first arterial air-trap chamber
4*b* second arterial air-trap chamber
5 venous air-trap chamber
6 duplex pump
7 ultrafiltration pump
8 pressurizing pump
9 degassing chamber
10 control device
11 evaluation device
12 liquid-level-adjusting device
13 liquid-level-adjusting device
a arterial puncture needle
b venous puncture needle
e only puncture needle (single needle)

The invention claimed is:

1. A blood purification apparatus comprising:
a blood circuit having a distal end and a puncture needle connectable to the distal end, blood of a patient being extracorporeally circulated through the blood circuit and the puncture needle; and
a blood purification device that purifies the blood flowing in the blood circuit,
wherein the blood purification apparatus performs blood purification treatment through the blood purification device while extracorporeally circulating the blood of the patient through the blood circuit with the puncture needle being stuck in an access vessel of the patient;
a pressure-change-producing device that applies a positive pressure or a negative pressure to a distal portion of the blood circuit while the puncture needle is yet to be connected to the blood circuit;
a pressure-change-detecting device that detects a pressure change in the distal portion of the blood circuit that occurs when the distal portion of the blood circuit that is under the positive pressure or the negative pressure applied by the pressure-change-producing device is connected to the puncture needle that is stuck in the patient; and
an evaluation device that evaluates a state of sticking of the puncture needle on the basis of the pressure change detected by the pressure-change-detecting device.

2. The blood purification apparatus according to claim 1, wherein the distal portion of the blood circuit is provided with a clamping device that is capable of closing a flow route, and wherein the pressure-change-detecting device, the clamping device, and the pressure-change-producing device perform the detection of the pressure change by closing the clamping device so as to close the distal portion of the blood circuit, applying the positive pressure or the negative pressure to the distal portion from the pressure-change-producing device, and opening the clamping device with the puncture needle being connected to the distal end.

3. The blood purification apparatus according to claim 1, wherein the pressure-change-producing device is a blood pump that is capable of delivering the blood of the patient through the blood circuit, and wherein the positive pressure or the negative pressure is applied to the distal portion of the blood circuit when the blood pump is activated.

4. The blood purification apparatus according to claim 1, wherein the pressure-change-producing device is a liquid-level-adjusting device that is configured to adjust a level of a liquid surface in an air-trap chamber provided to the blood circuit by introducing or discharging air into or from the air-trap chamber, and to apply the positive pressure or the negative pressure is applied to the distal portion of the blood circuit when the liquid-level-adjusting device is activated.

5. The blood purification apparatus according to claim 1, wherein the pressure-change-producing device is an ultra-filtration pump for removing water from the blood flowing in the blood purification device, and wherein the positive pressure or the negative pressure is applied to the distal portion of the blood circuit when the ultrafiltration pump is activated.

6. The blood purification apparatus according to claim 1, wherein the pressure-change-detecting device is a pressure sensor that is capable of detecting a hydraulic pressure in the blood circuit.

7. The blood purification apparatus according to claim 1, wherein the pressure-change-producing device is activated with the flow route provided by the blood circuit being filled with a priming solution after priming of the blood circuit is performed.

8. The blood purification apparatus according to claim 1, wherein the blood circuit includes an arterial blood circuit with a distal end and a venous blood circuit with a distal end, and the puncture needle is an only puncture needle that is connected to the distal end of the arterial blood circuit and the distal end of the venous blood circuit.

9. The blood purification apparatus according to claim 8, wherein the arterial blood circuit and the venous blood circuit are connected together by a wye.

10. The blood purification apparatus according to claim 1, wherein the blood circuit includes an arterial blood circuit with a distal end and a venous blood circuit with a distal end, the distal end of the arterial blood circuit including a joint and the distal end of the venous blood circuit includes a joint and the puncture needle connects to the distal end of the arterial blood circuit, the distal end of the venous blood circuit, or both to the puncture needle.

11. The blood purification apparatus of claim 10, wherein the joint of the arterial blood circuit, the joint of the venous blood circuit, or both are locked to the puncture needle by a lock ring.

12. The blood purification apparatus of claim 6, wherein the blood circuit includes an arterial blood circuit and the pressure sensor is located in the arterial blood circuit and the arterial blood circuit includes a first arterial air-trap chamber that detects the pressure change for blood removal.

13. The blood purification apparatus of claim 12, wherein the arterial blood circuit includes a second arterial air-trap chamber and a pressure sensor is located within the arterial blood circuit that detects pressure at an inlet of a dialyzer.

14. The blood circuit purification apparatus of claim 13, wherein the blood circuit includes a venous blood circuit and the venous blood circuit includes a venous air-trap chamber and a pressure sensor that detects venous pressure of the venous blood circuit.

15. The blood purification apparatus of claim 12, wherein the pressure sensor detects a pressure in an air layer of the first arterial air-trap chamber.

16. The blood purification apparatus of claim 12, wherein the pressure sensor in the venous blood circuit detects a pressure in an air layer of the venous blood circuit.

\* \* \* \* \*